United States Patent
Greenwald et al.

(10) Patent No.: US 7,462,687 B2
(45) Date of Patent: Dec. 9, 2008

(54) PRODRUGS OF VANCOMYCIN WITH HYDROLYSIS RESISTANT POLYMER LINKAGES

(75) Inventors: Richard B. Greenwald, Somerset, NJ (US); Hong Zhao, Edison, NJ (US)

(73) Assignee: Enzon Pharmaceuticals, Inc., Bridgewater, NJ (US)

( * ) Notice: Subject to any disclaimer, the term of this patent is extended or adjusted under 35 U.S.C. 154(b) by 492 days.

(21) Appl. No.: 10/705,740

(22) Filed: Nov. 11, 2003

(65) Prior Publication Data

US 2004/0142858 A1 Jul. 22, 2004

Related U.S. Application Data

(60) Provisional application No. 60/425,890, filed on Nov. 12, 2002, provisional application No. 60/425,892, filed on Nov. 12, 2002.

(51) Int. Cl.
*A61K 38/14* (2006.01)

(52) U.S. Cl. .................................................. 530/322

(58) Field of Classification Search .................. None
See application file for complete search history.

(56) References Cited

U.S. PATENT DOCUMENTS

| 5,681,811 A | 10/1997 | Ekwuribe | |
|---|---|---|---|
| 6,180,095 B1 * | 1/2001 | Greenwald et al. | 424/85.1 |
| 2002/0103259 A1 * | 8/2002 | Martinez et al. | 514/617 |

FOREIGN PATENT DOCUMENTS

| WO | WO 97/04796 | | 2/1997 |
|---|---|---|---|
| WO | WO 03/040211 | A2 | 5/2003 |

* cited by examiner

*Primary Examiner*—Thomas S Heard
(74) *Attorney, Agent, or Firm*—Lucas & Mercanti, LLP

(57) ABSTRACT

Vancomycin-polymer conjugates are disclosed. In preferred aspects, polymer residues which are hydrolysis resistant in vitro, are selectively attached to the sugar amino and/or N-methyl amino groups of vancomycin and related compounds. Vancomycin-polymer conjugates made by the methods and methods of treatment using the conjugates are also disclosed.

28 Claims, 5 Drawing Sheets

2

3

PRODRUGS OF VANCOMYCIN WITH HYDROLYSIS RESISTANT POLYMER LINKAGES

CROSS REFERENCE TO RELATED APPLICATION

This application claims the benefit of priority from U.S. provisional patent application Nos. 60/425,890 and 60/425,892, each filed Nov. 12, 2002. The contents of each application are incorporated herein by reference.

FIELD OF THE INVENTION

The present invention relates to polymeric derivatives of vancomycin. More particularly, the invention relates to select vancomycin derivatives in which the sugar amino group and/or the N-methyl amino group has been modified with a substantially non-antigenic polymer through a hydrolysis resistant linker.

BACKGROUND OF THE INVENTION

Vancomycin is an antibiotic which was initially discovered in the 1950's, see U.S. Pat. No. 3,067,099. It is usually reserved for use in the treatment of severe gram positive infections such as those caused by Staphylococcus aureus and when traditional antibiotics have failed. Over the years, there have been several proposals for improving one or more attributes of vancomycin, usually by continuous infusion. In another example, prodrugs of vancomycin have been proposed as a way of increasing the solubility and circulating life of the drug.

Prodrugs include chemical derivatives of a biologically-active parent compound which, upon administration, will eventually liberate the active parent compound in vivo. The use of prodrugs allows the artisan to modify one or more properties such as the onset and/or duration of action of a biologically-active compound in vivo. Prodrugs are often biologically inert or substantially inactive forms of the active compound. The rate of release of the active drug is influenced by several factors including the rate of hydrolysis of the linker which joins the parent biologically active compound to the prodrug carrier.

Polymer conjugates of vancomycin have also been proposed as potential prodrugs. For example, commonly-assigned U.S. Pat. No. 6,180,095 discloses benzyl elimination (BE) systems as part of a tripartite polymer-based prodrug platform. These BE prodrug systems are designed inter alia to releasably attach polymers such as polyethylene glycol (hereinafter PEG) to hydroxyl or amine residues on small molecules. After administration to a patient, the prodrugs break down in a predictable fashion. First, the polymer portion hydrolyzes at a predictable, predetermined rate due to the presence of selected bifunctional linkers which contain the desired "trigger". Once the polymer portion has been hydrolyzed, the BE system is initiated or triggered and rapidly releases the parent compound. Commonly assigned U.S. Pat. Nos. 5,965,119 and 6,303,569 disclose related tripartate prodrug systems containing trimethyl lock triggers. Commonly assigned U.S. Patent application 60/425,892 discloses mono and di-substituted polymeric prodrugs employing releasably linked platforms. Commonly assigned U.S. Pat. No. 6,395,266 discloses a branched polymeric platform system useful for multiple loading of biologically active moieties. Commonly assigned U.S. Pat. Nos. 6,127,355 and 5,965,566 disclose high molecular weight polymer conjugates as drug delivery systems. Commonly assigned U.S. Patent Applications 60/425,890 and 60/425,892 disclose methods of making releasable polymeric vancomycin derivatives. In the aforementioned applications, the polymer platform is attached at either one or both of the sugar amine group and the N-methyl amine group of the vancomycin or vancomycin derivative. The disclosure of each of the above-mentioned commonly-assigned patents and applications is incorporated herein by reference.

In spite of the fact that vancomycin is listed among the various biologically active compounds having an available amino group for attachment of the prodrug platform in each of the foregoing commonly-assigned patents, further advances have been sought to refine and improve vancomycin therapies. In the past, it was thought that using permanent bonds, i.e. those substantially resistant to hydrolysis, to attach the vancomycin to a polymer such as PEG would not provide sufficiently active compounds. It has now been discovered that attachment of polymeric platforms through amide, urea, carbamate or other similar hydrolysis-resistant bonds is advantageous and can provide additional prodrugs. The vancomycin prodrugs of the present invention, have been shown to hydrolyze and liberate vancomycin in vivo over an extended period of time. Advantages of these types of prodrugs include, extended circulating life due to very slow hydrolysis of the polymer portion to release native drug and a more efficient cost effective manufacturing process. New versions of prodrugs capable of maintaining efficacy and reducing negative side effects while maintaining cost effectiveness is an ongoing need. This invention addresses such needs.

SUMMARY OF THE INVENTION

In one aspect of the invention, a compound of the formula (I) is provided:

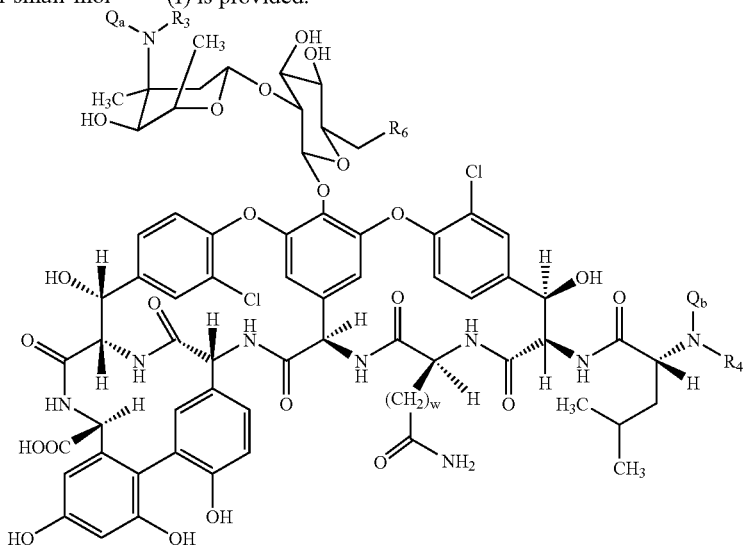

wherein:

R$_3$-R$_5$ are each independently selected from among hydrogen, C$_{1-6}$ alkyls, C$_{3-12}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ alkenyls, C$_{3-12}$ branched alkenyls, C$_{1-6}$ alkynyls, C$_{3-12}$ branched alkynyls, C$_{1-6}$ heteroalkyls, substituted C$_{1-6}$ heteroalkyls, C$_{1-6}$ alkoxyalkyl, phenoxyalkyl and C$_{1-6}$ heteroalkoxys;

R$_6$ is OH, NH-aryl, NH-aralkyl, or NH—C$_{1-12}$ alkyl;

w is 1 or 2;

Q$_a$ is H or a residue of the formula:

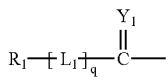

wherein:

R$_1$ is a polymer residue;

Y$_1$ is O, S or NR$_5$, and

L$_1$ is a hydrolysis resistant bifunctional linker;

q is 0 or a positive integer; and

Q$_b$ is H or a residue of the formula:

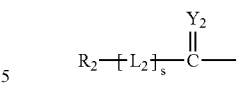

wherein:

R$_2$ is a polymer residue;

Y$_2$ is O, S or NR$_5$, and

L$_2$ is a hydrolysis resistant bifunctional linker;

s is 0 or a positive integer;

provided that Q$_a$ and Q$_b$ are both not simultaneously H.

In others aspect of the invention the polymeric residue (R$_1$) or (R$_2$) includes both an alpha and an omega terminal linking group so that two equivalents of the vancomycin residue are delivered. An example of such a bifunctional polymer conjugate is illustrated below as formulas (II) and (III):

(i)-R$_1$-(i)  (II)

and (ii)-R$_2$-(ii)  (III)

wherein (i) is

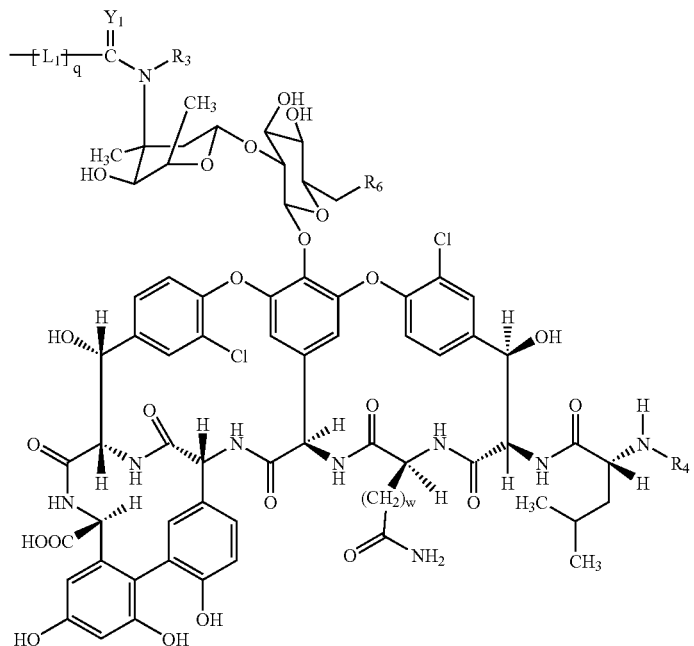

and (ii) is

-continued

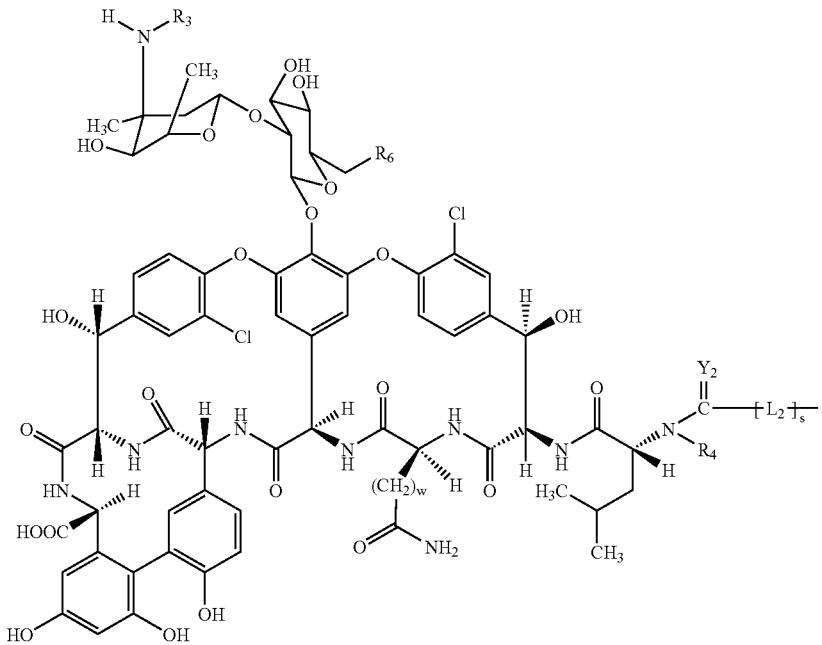

wherein all variables are as described above.

Another aspect of the invention includes methods of treating vancomycin susceptible diseases in mammals, i.e. a human, comprising administering a compound of the formula (I) to a mammal in need of such treatment, whereby, the vancomycin-based compound of formula (I) undergoes degradation and releases vancomycin or vancomycin derivative in vivo.

For purposes of the present invention, the term "residue" shall be understood to mean that portion of a vancomycin compound or bifunctional linker which remains after it has undergone a substitution reaction.

For purposes of the present invention, the term "polymer residue" or "PEG residue" shall each be understood to mean that portion of the polymer or PEG which remains after it has undergone a reaction with a vancomycin compound such as those described herein as being of formula (I).

For purposes of the present invention, the term "alkyl" shall be understood to include straight, branched, substituted, e.g. halo-, alkoxy-, nitro-, $C_{1-12}$ alkyls, $C_{3-8}$ cycloalkyls or substituted cycloalkyls, etc. Positive integer shall mean an integer greater than or equal to one, preferably between 1 and 10 and more preferably 1.

For purposes of the present invention, the term "substituted" shall be understood to include adding or replacing one or more atoms contained within a functional group or compound with one or more different atoms.

For purposes of the present invention, substituted alkyls include carboxyalkyls, aminoalkyls, dialkylaminos, hydroxyalkyls and mercaptoalkyls; substituted alkenyls include carboxyalkenyls, aminoalkenyls, dialkenylaminos, hydroxyalkenyls and mercaptoalkenyls; substituted alkynyls include carboxyalkynyls, aminoalkynyls, dialkynylaminos, hydroxyalkynyls and mercaptoalkynyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthienyl; substituted heteroalkyls include moieties such as 3-methoxy-thienyl; alkoxy includes moieties such as methoxy; and phenoxy includes moieties such as 3-nitrophenoxy. Halo- shall be understood to include fluoro, chloro, iodo and bromo.

The term "sufficient amounts" for purposes of the present invention shall mean an amount which achieves a desired effect or therapeutic effect as such effect is understood by those of ordinary skill in the art.

One advantage of the compounds of the invention is that vancomycin conjugate has an extended circulating life. There is also provided a means for controlling the rate of hydrolysis of the derivative. Thus, the artisan has the ability to include varied substituents that allow for modulation of the rate of hydrolysis of the prodrug to optimize the pK profile, reduce dose frequency and its related medical costs. The modifications described herein also allow one to maintain serum levels and prevent bacterial resistance of vancomycin from developing.

The conjugates made by the methods of the invention also provide an economic advantage in the manufacturing process using high molecular weight polymers.

Other and further advantages will be apparent from the following description and drawings.

DETAILED DESCRIPTION

A. Formula (I)

Figure 1:
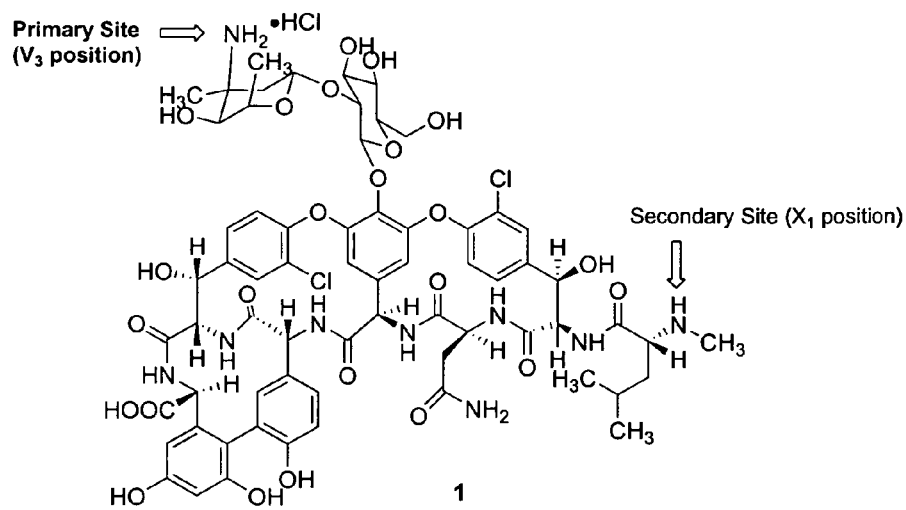
FIGS. 1-5 schematically illustrate methods of forming compounds of the present invention which are described in the Examples.
Figure 1:
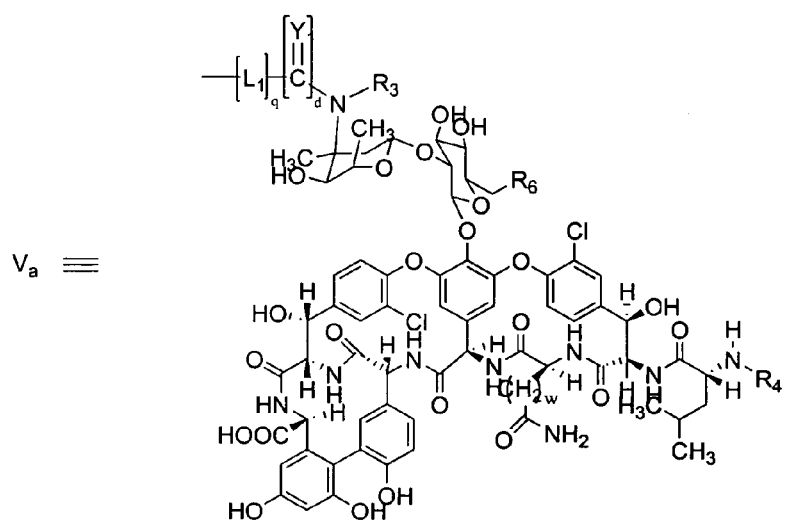
Figure 1:
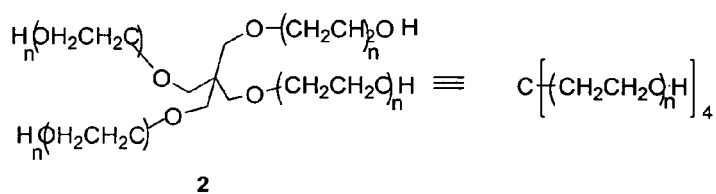
Figure 1:
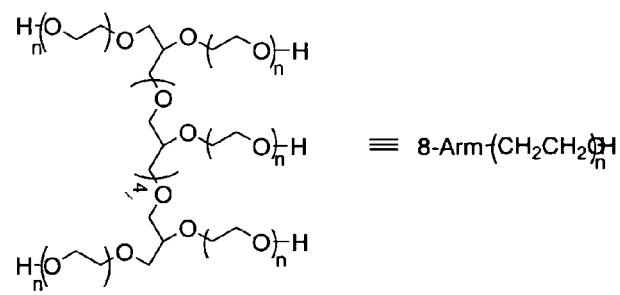

In one aspect of the invention compounds of the formula (I) are provided:

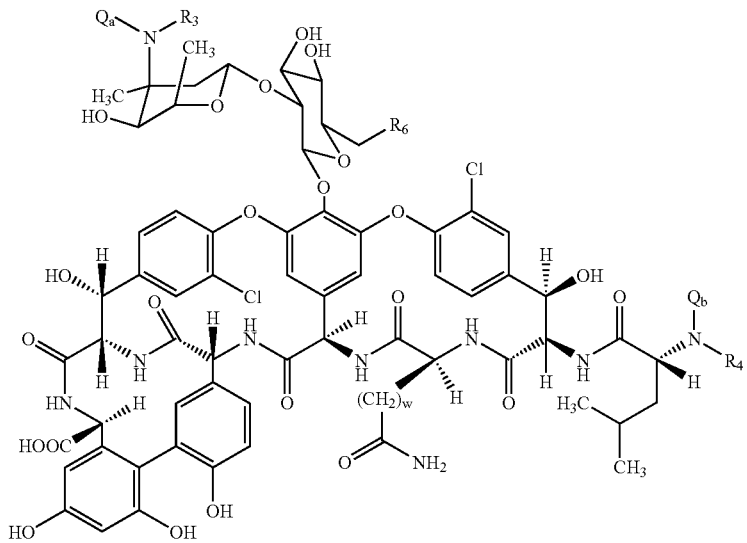

wherein:

$R_3$-$R_5$ are each independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ alkenyls, $C_{3-12}$ branched alkenyls, $C_{1-6}$ alkynyls, $C_{3-12}$ branched alkynyls, $C_{1-6}$ heteroalkyls, substituted $C_{1-6}$ heteroalkyls, $C_{1-6}$ alkoxyalkyl, phenoxyalkyl and $C_{1-6}$ heteroalkoxys;

$R_6$ is OH, NH-aryl, NH-aralkyl, or NH—$C_{1-12}$ alkyl;
w is 1 or 2;

$Q_a$ is H or a residue of the formula:

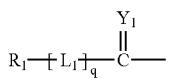

wherein:

$R_1$ is a polymer residue;
$Y_1$ is O, S or $NR_5$;
$L_1$ is a hydrolysis resistant bifunctional linker;
q is 0 or a positive integer; and
$Q_b$ is H or a residue of the formula:

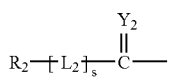

wherein:

$R_2$ is a polymer residue;
$Y_2$ is O, S or $NR_5$;
$L_2$ is a hydrolysis resistant bifunctional linker; and
s is 0 or a positive integer;
provided that $Q_a$ and $Q_b$ are both not simultaneously H.

In another aspect of the invention $R_1$ can further comprise a capping group J selected from the group consisting of OH, $NH_2$, SH, $CO_2H$, $C_{1-6}$ alkyl moieties, and a compound of the formula (i),

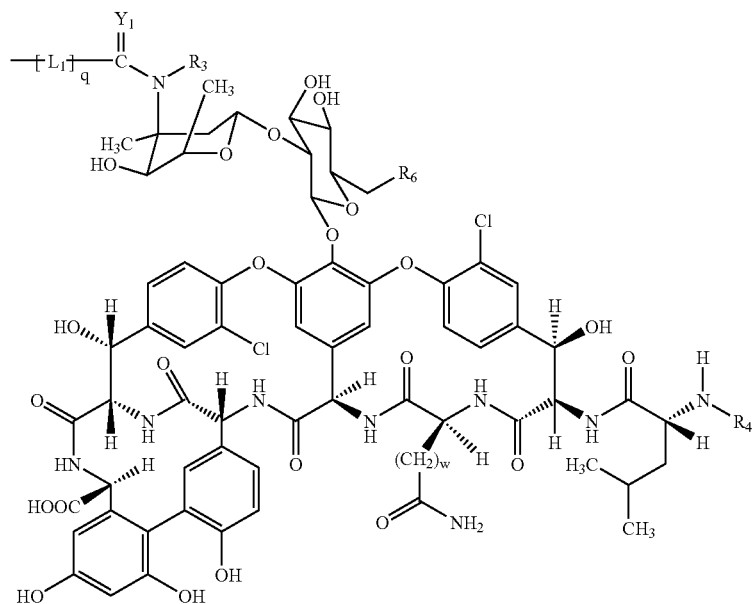
In another aspect of the invention $R_2$ can further comprise a capping group J selected from the group consisting of OH, $NH_2$, SH, $CO_2H$, $C_{1-6}$ alkyl moieties, and a compound of the formula (ii),
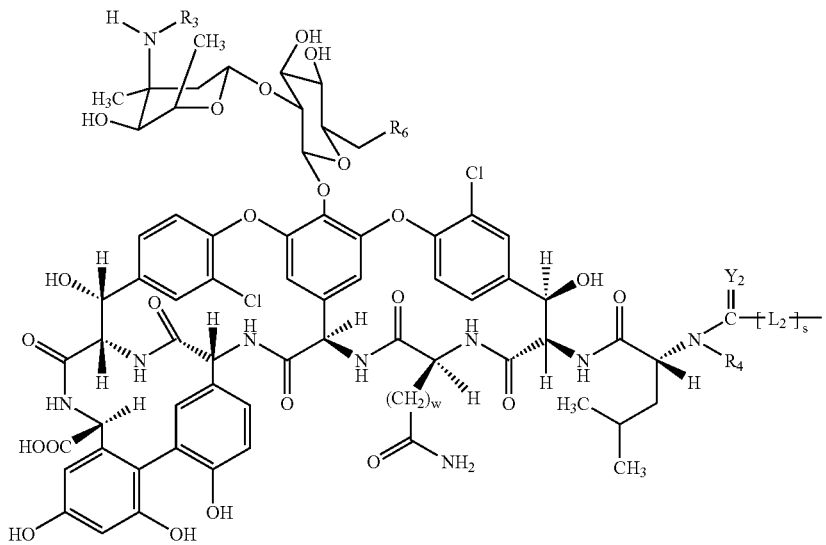
wherein all variable are as described above.

This aspect of the invention allows for bifunctional compounds that are formed when the polymeric residue ($R_1$) or ($R_2$) includes both an alpha and an omega terminal linking group so that two equivalents of the vancomycin residue is delivered. An example of such a bifunctional polymer conjugate is illustrated below as formulas (II) and (III):

$$(i)\text{-}R_1\text{-}(i) \quad (II)$$

and $$(ii)\text{-}R_2\text{-}(ii) \quad (III)$$

wherein (i) is

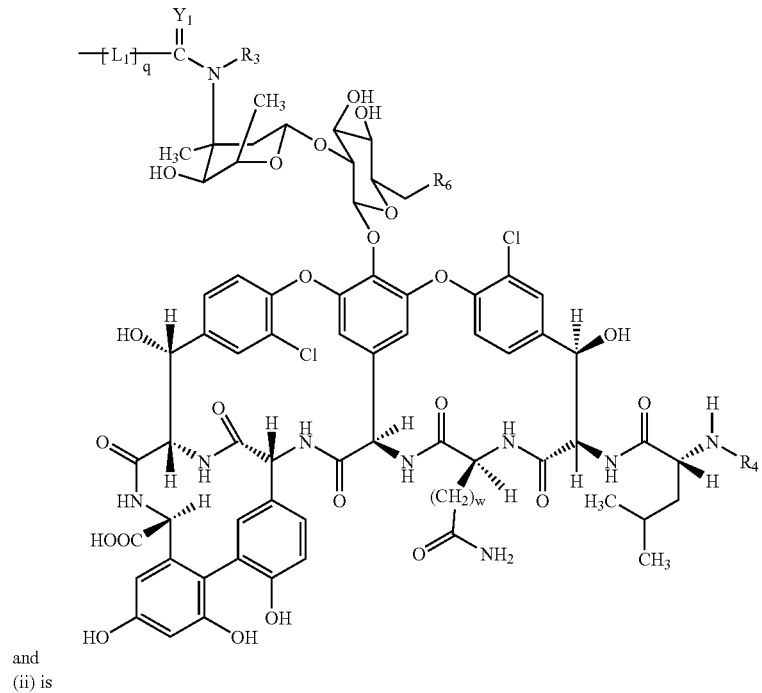

and
(ii) is

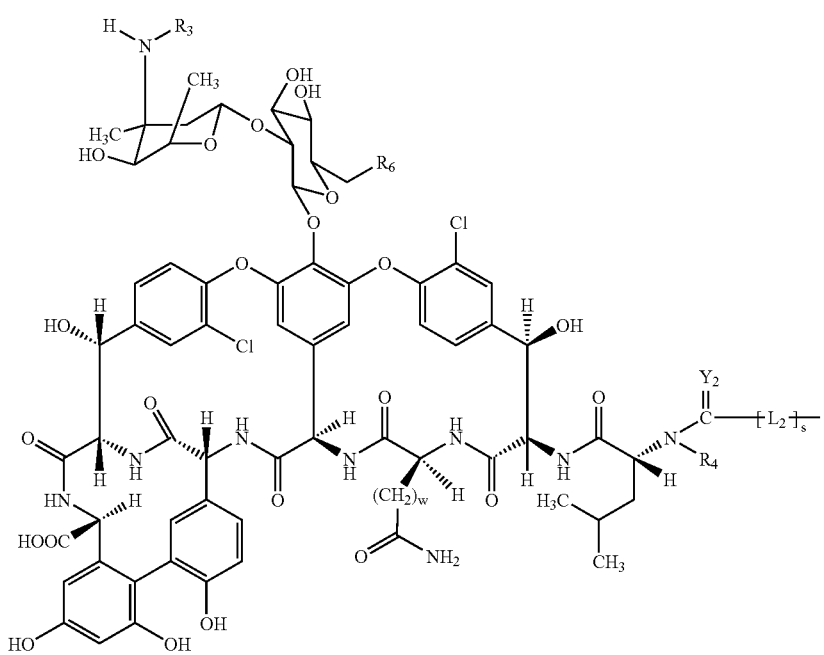

wherein all variables are as described above.

For the compounds of Formula (I) the following are preferred,
Y$_1$ and Y$_2$ are independently O;
R$_3$ and R$_4$ are each independently selected from among hydrogen, or CH$_3$;
R$_6$ is OH or NH-aryl;
q and s are independently 0-2, and
w is 1.

While the above formula (I) covers many of the more well known vancomycin-type compounds known to have biological activity, it is to be understood that the invention embraces not only these specific compounds, but also those vancomycin-based compounds know to artisans of ordinary skill to have a sugar amino group. For example, the inventive processes described herein can also be carried out with the vancomycin derivatives described in, for example, EP 0 201 251, "The Role of Hydrophobic Substituents in the Biological Activity of Glycopeptide Antibiotics", *J. Am. Chem Soc.* 2000, 122, 12608-12609 and U.S. Pat. Nos. 4,495,179, 3,067,099, 4,556,008, 4,548,925 and 4,547,488 to name but a few. The disclosure of each of the foregoing is incorporated herein by reference. In most preferred aspects of the invention, however, the vancomycin compound employed for the processes described herein is of the formula (V):

R$_7$ is selected from among hydrogen, C$_{1-6}$ alkyls, C$_{2-6}$ alkenyls, C$_{2-6}$ alkynyls, C$_{3-12}$ branched alkyls, C$_{3-8}$ cycloalkyls, C$_{1-6}$ substituted alkyls, C$_{2-6}$ substituted alkenyls, C$_{2-6}$ substituted alkynyls, C$_{3-8}$ substituted cycloalkyls, aryls substituted aryls, aralkyls, C$_{1-6}$ heteroalkyls, substituted C$_{1-6}$ heteroalkyls, C$_{1-6}$ alkoxyalkyl, phenoxyalkyl and C$_{1-6}$ heteroalkoxy, and J is a capping group as described above with regard to formulas (II) and (III).

For illustrative purposes, in the case of multiple arm polyethylene glycol (PEG) residues, examples of possible conjugates are selected from among:

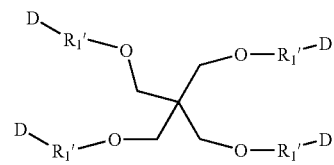

(V)

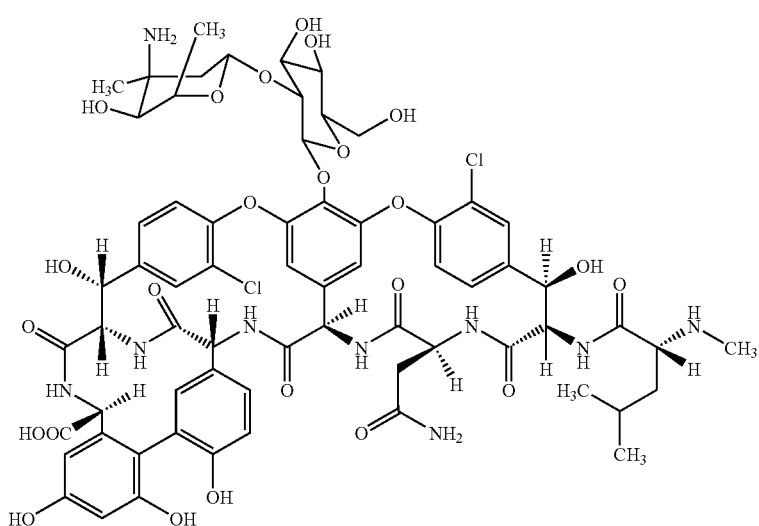

B. Polymer Residues

As stated above, R$_1$ and R$_2$ are polymer residues. Preferably R$_1$ and R$_2$ are water soluble linear, branched or multiple arm polymer residues which are preferably substantially non-antigenic such as polyalkylene oxide (PAO's) and more preferably polyethylene glycol. For purposes of illustration and not limitation, the linear polyethylene glycol (PEG) residue portion of R$_1$ and R$_2$ can be selected from among:

J-O—(CH$_2$CH$_2$O)$_x$—
J-O—(CH$_2$CH$_2$O)$_x$—CH$_2$C(O)—O—,
J-O—(CH$_2$CH$_2$O)$_x$—CH$_{2CH2}$NR$_7$—,
J-O—(CH$_2$CH$_2$O)$_x$—CH$_2$CH$_2$SH—,
—OC(O)CH$_2$—O—(CH$_2$CH$_2$O)$_x$—CH$_2$C(O)—O—,
—NR$_7$CH$_2$CH$_2$—O—(CH$_2$CH$_2$O)$_x$—CH$_2$CH$_2$NR$_7$— and
—SHCH$_2$CH$_2$—O—(CH$_2$CH$_2$O)$_x$—CH$_2$CH$_2$SH—.

wherein:
x is the degree of polymerization;

-continued

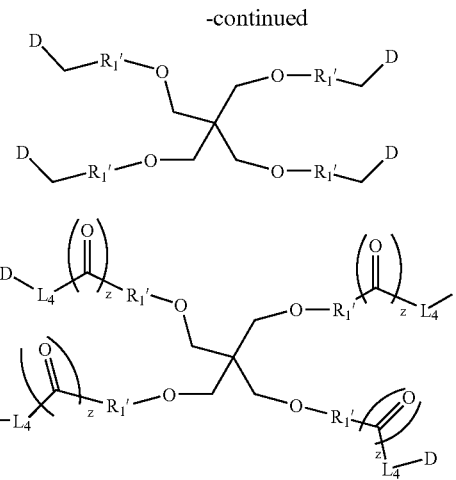

and

-continued

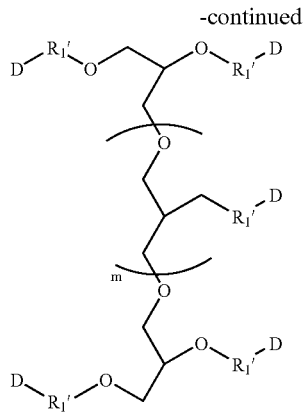

wherein
m is 0-4;
z is 0 or 1;
$L_4$ is the same as that which defines $L_{1-3}$;
D is a moiety of the formula $V_a$ or $V_b$;
$R_1' =$
—$(CH_2CH_2O)_x$—;
—$(CH_2CH_2O)_x$—$CH_2C(O)$—;
—$(CH_2CH_2O)_x$—$CH_2CH_2NR_7$—, and
—$(CH_2CH_2O)_x$—$CH_2CH_2SH$—;
wherein x is a positive integer;
$R_{3-4}$ are independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ alkenyls, $C_{3-12}$ branched alkenyls, $C_{1-6}$ alkynyls, $C_{3-12}$ branched alkynyls, $C_{1-6}$ heteroalkyls, substituted $C_{1-6}$ heteroalkyls, $C_{1-6}$ alkoxyalkyl, phenoxyalkyl and $C_{1-6}$ heteroalkoxys;

$V_a$ is

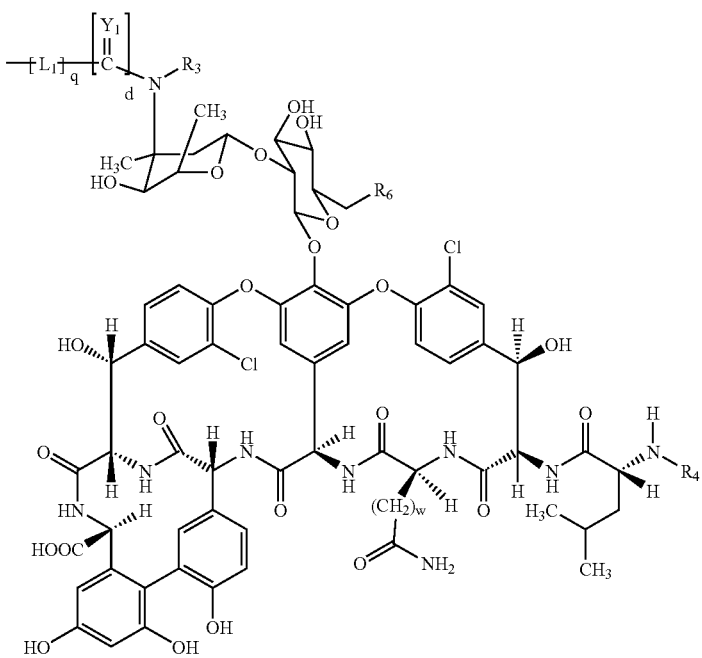

and $V_b$ is

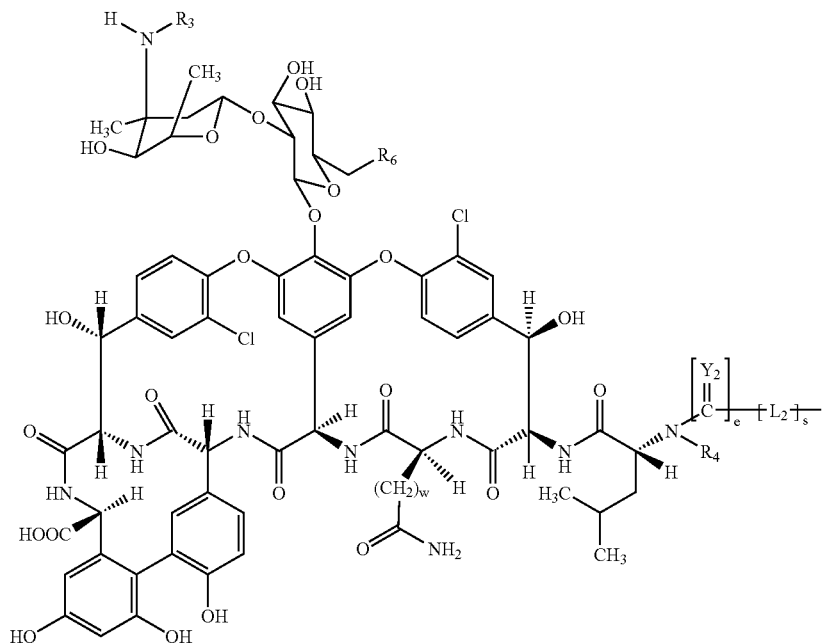

wherein, d, e, q, and s are each independently 0 or 1, and all other variables are as described above.

Preferably, $R_{3-4}$ are independently selected from among hydrogen and $C_{1-6}$ alkyls; n is 1-400, more preferably 50-250, and m is 0-20, more preferably 0-4.

The multiple arm polymeric residues, allow for multiple points of attachment thereby increasing the loading of the vancomycin or vancomycin derivative residues.

In one particularly preferred embodiment, $R_1$ and $R_2$ are selected from among

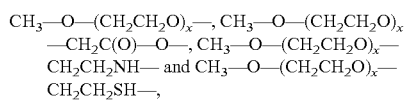

where x is a positive integer, selected so that the total weight average molecular weight is from about 5,000 to about 100,000 Da. Preferably, the total weight average molecular weight is from about 10,000 to about 80,000 Da, with from about 20,000 to about 40,000 Da being more preferred. The most preferable total molecular weight of the polymer is 40,000 Da depending upon the needs of the artisan.

In a more preferred embodiment, in the case of multiple arm polyethylene glycol (PEG) residues, possible conjugates are selected from among:

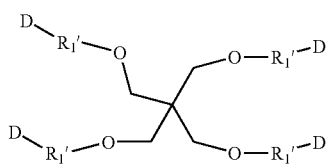

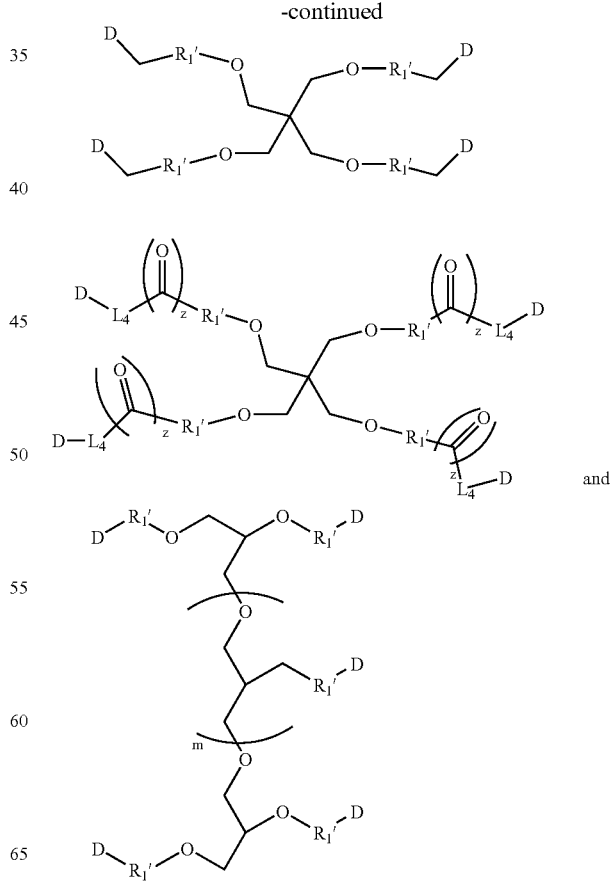

and wherein

R$_{3-4}$ are independently selected from among hydrogen, and C$_{1-6}$ alkyls;

z is 0 or 1;

n is 50-250;

m is 0-4; and

D is V$_a$ or V$_b$ as described above.

Preferably, the total molecular weight range of the multiple arm polymer residue is 20,000 Da to 40,000 Da.

Also contemplated within scope of the invention are terminally branched polymer conjugates such as those compounds described in commonly assigned PCT publication numbers WO02/065988 and WO02/066066, the disclosure of each being incorporated herein by reference. Within these general formulae, the following are preferred:

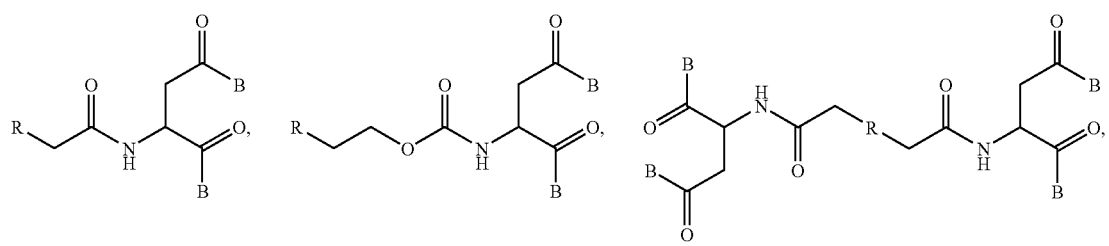

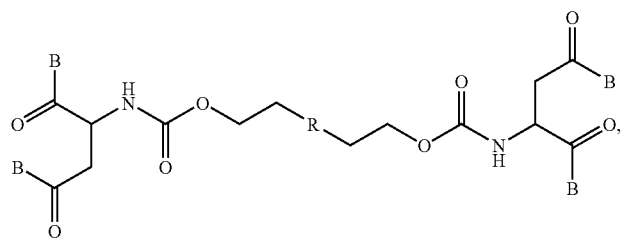

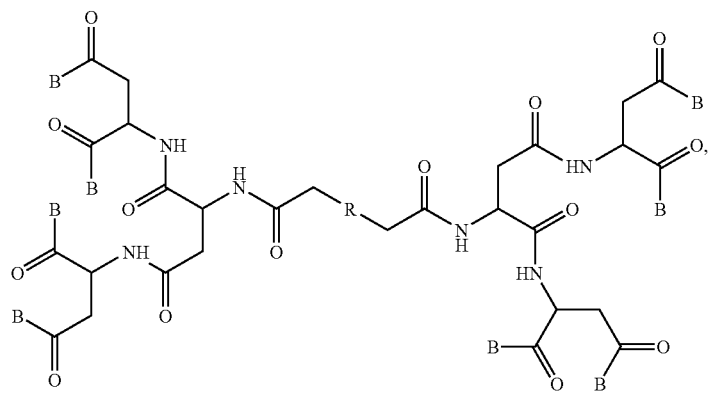

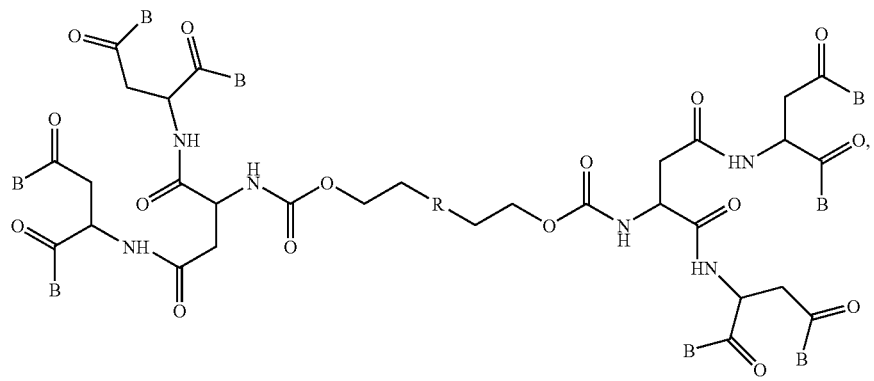

-continued

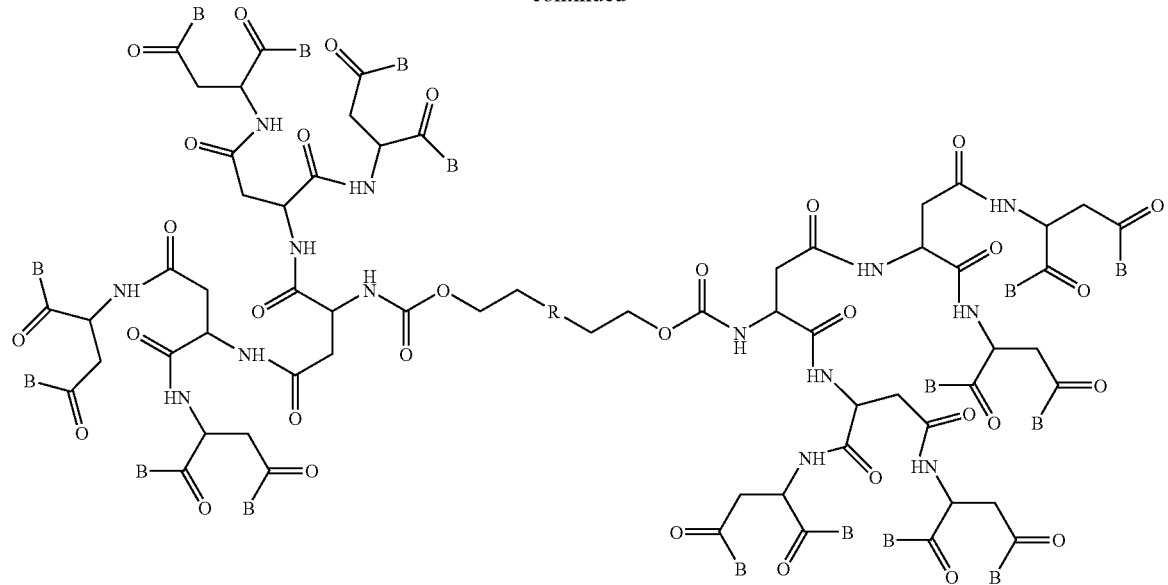

and

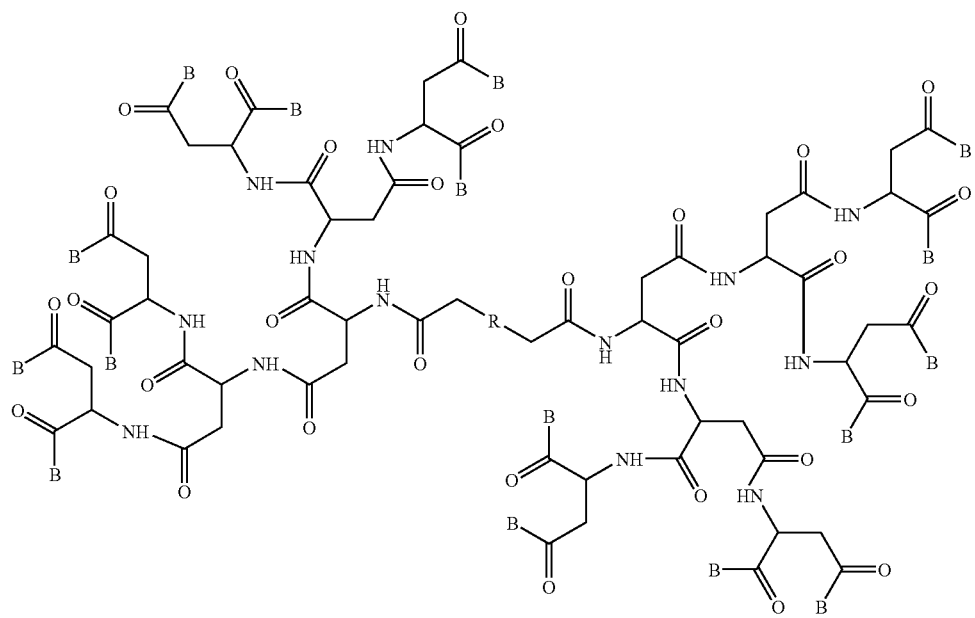

where R is a linear polymeric residue such as those described above for $R_1$ and $R_2$, and B is a moiety of the formula:

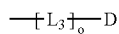

wherein
$L_3$ is the same as that which describes $L_1$ and $L_2$;
o is 0 or 1; and
D is a moiety of formula $V_a$ or $V_b$.

Additionally, branched polymer residues such as those compounds described in commonly assigned U.S. Pat. Nos. 5,643,575; 5,919,455 and 6,113,906, the disclosure of each being incorporated herein by reference are also contemplated within the scope of the nvention. These residues allow for the following preferred conjugates to be formed:

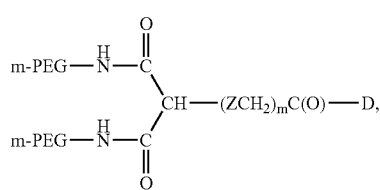

-continued

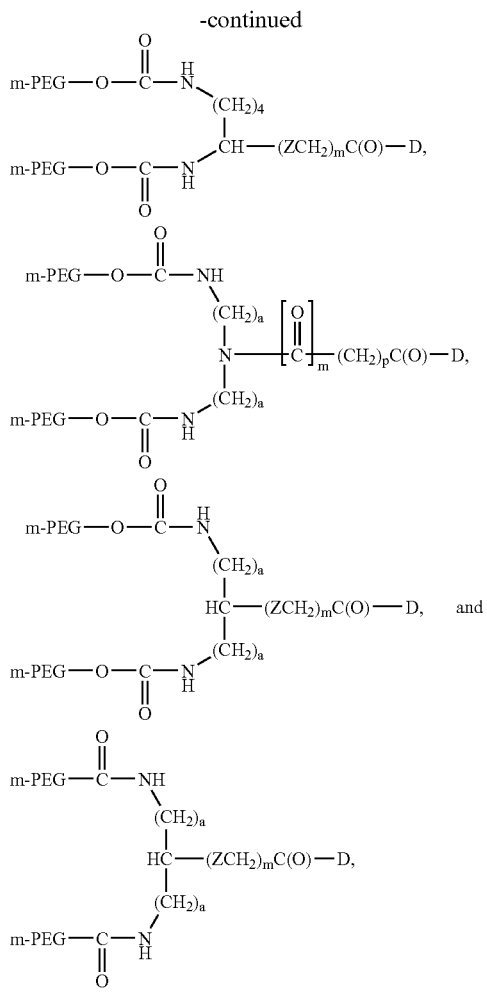

wherein:
(a) is an integer of from about 1 to about 5;
Z is O, $NR_8$, S, SO or $SO_2$; where $R_8$ is H, $C_{1-8}$ alkyl, $C_{1-8}$ branched alkyl, $C_{1-8}$ substituted alkyl, aryl or aralkyl;
(m) is 0 or 1;
(p) is a positive integer, preferably from about 1 to about 6, and
D is a moiety of formula $V_a$ or $V_b$.
PEG is generally represented by the structure:

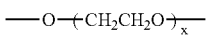

and $R_1$ and $R_2$ preferably comprise residues of this formula.

The degree of polymerization for the polymer (x) can be from about 10 to about 2,300. This represents the number of repeating units in the polymer chain and is dependent on the molecular weight of the polymer. The (J) moiety is a capping group as defined herein, i.e. a group which is found on the terminal of the polymer and, in some aspects, can be selected from any of $NH_2$, OH, SH, $CO_2H$, $C_{1-6}$ alkyls or other PEG terminal activating groups, as such groups are understood by those of ordinary skill.

Branched PEG derivatives such as those described in commonly-assigned U.S. Pat. No. 5,643,575 (the '575 patent), "star-PEG's" and the "multi-armed PEGs" such as those shown above and described in Nektar Corporation's 2003 catalog "Polyethylene Glycol and Derivatives for Advanced PEGylation" are useful in the methods of the invention. The disclosure of each of the foregoing is incorporated herein by reference. The branching afforded by the '575 patent allows secondary or tertiary branching as a way of increasing polymer loading on a biologically active molecule or enzyme from a single point of attachment. It will be understood that the water-soluble polymer can be functionalized for attachment to the bifunctional linkage groups if required without undue experimentation.

Although PAO's and PEG's can vary substantially in weight average molecular weight, preferably, $R_1$ and $R_2$ have a total weight average molecular weight of from about 20,000 to about 40,000 Da in most aspects of the invention.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

In a further embodiment, and as an alternative to PAO-based polymers, $R_1$ and $R_2$ are optionally selected from among one or more effectively non-antigenic materials such as dextran, polyglutamic acid, polyaspartic acid, polyhydroxyethyl-aspartate (poly-HEA), chitans, polyvinyl alcohols, carbohydrate-based polymers, hydroxypropylmethylacrylamide (HPMA), polyalkylene oxides, and/or copolymers thereof. See also commonly-assigned U.S. Pat. No. 6,153,655, the contents of which are incorporated herein by reference. It will be understood by those of ordinary skill that the same type of activation is employed as described herein as for PAO's such as PEG. Those of ordinary skill in the art will further realize that the foregoing list is merely illustrative and that all polymeric materials having the qualities described herein are contemplated and that other polyalkylene oxide derivatives such as the polypropylene glycols, etc. are also contemplated.

C. Hydrolysis Resistant Linkers

In many aspects of the invention, and formula (I) in particular, $L_{1-3}$ are hydrolysis resistant bifunctional linking groups which facilitate attachment of the vancomycin or vancomycin derivative to the polymer strands, i.e. $R_1$ and $R_2$. The linkage provided can be either direct or through further coupling groups known to those of ordinary skill. In this aspect of the invention, $L_{1-3}$ can be selected from among:

—$[C(O)]_v NR_{25}(CR_{26}R_{27})_t$—
—$[C(O)]_v (CR_{26}R_{27})_t$—
—$[C(O)]_v NR_{25}(CR_{26}R_{27}O)_t$—
—$[C(O)]_v NR_{25}(CR_{26}R_{27})_t$—
—$[C(O)]_v NR_{25}(CR_{26}R_{27}O)_t(CR_{28}R_{29})_yO$—
—$[C(O)]_v NR_{25}(CR_{26}R_{27}O)_t(CR_{28}R_{29})_y$—
—$[C(O)]_v NR_{25}(CR_{26}R_{27})_tO$—
—$[C(O)]_v NR_{25}(CR_{26}R_{27})_t(CR_{28}CR_{29}O)_yNR_{30}$—
—$[C(O)]_v O(CR_{26}R_{27})_tNR_{30}$—
—$[C(O)]_v O(CR_{26}R_{27})_tO$—
—$[C(O)]_v NR_{25}(CR_{26}R_{27})_tNR_{30}$—
—$[C(O)]_v NR_{25}(CR_{26}R_{27})_t(CR_{28}CR_{29}O)_y$—
—$[C(O)]_v NR_{25}(CR_{26}CR_{27}O)_t$—
—$[C(O)]_v NR_{25}(CR_{26}CR_{27}O)_t(CR_{28}R_{29})_yNR_{30}$—
—$[C(O)]_v NR_{25}(CR_{26}CR_{27}O)_t$—
—$[C(O)]_v O(CR_{26}R_{27})_t$—$NR_{30}$—
—$[C(O)]_v$—$O(CR_{26}R_{27})_tNR_{30}$—
—$[C(O)]_v O(CR_{26}R_{27})_tO$—
—$[C(O)]_v O(CR_{26}CR_{27}O)_tNR_{30}$—

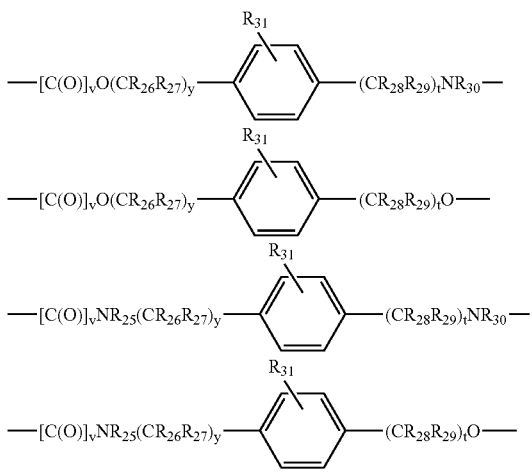

wherein:

$R_{25}$-$R_{30}$ are independently selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyl $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ hetero-alkyls, $C_{1-6}$ alkoxyalkyl, phenoxyalkyl and $C_{1-6}$ hetero-alkoxys; and $R_{31}$ is selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ sub-stituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy-alkyl, phenoxyalkyl and $C_{1-6}$ heteroalkoxys, $NO_2$, haloalkyl and halogen;

t and y are individually selected positive integers, preferably from about 1 to about 4, and v is 0 or 1.

In other aspects of the invention, $L_{1-3}$ can independently include an amino acid residue. The amino acid can be selected from any of the known naturally-occurring L-amino acids, e.g., alanine, valine, leucine, isoleucine, glycine, serine, threonine, methionine, cysteine, phenylalanine, tyrosine, tryptophan, aspartic acid, glutamic acid, lysine, arginine, histidine, proline, and/or a combination thereof, to name but a few.

The amino acid residues are preferably of the formula

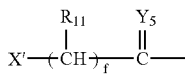

wherein X' is O, S or $NR_9$, $Y_5$ is O, S or $NR_{10}$, and $R_9$, $R_{10}$ and $R_{11}$ are independently selected from the same group as that which defines $R_3$ but each is preferably H or lower alkyl (i.e. $C_{1-6}$ alkyl); and f is a positive integer from about 1 to about 10, preferably 1.

Desirable amino acid residues include all of the known naturally-occurring L-amino acids. For example, L-isoleucine as a transport enhancer is exemplified in the Examples provided below. Surprisingly, it has also been discovered that D-amino acids are useful as transport enhancers, e.g., both D and L-alanine, and other analogous amino acid optical isomers, show the same activity. Derivatives and analogs of the naturally occurring amino acids, as well as various art-known non-naturally occurring amino acids (D or L), hydrophobic or non-hydrophobic, are also contemplated to be within the scope of the invention. Simply by way of example, amino acid analogs and derivates include: 2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2-diaminopimelic acid, 2,3-diaminopropionic acid, n-ethylglycine, N-ethylasparagine, 3-hydroxyproline, 4-hydroxyproline, isodesmosine, allo-isoleucine, N-methylglycine, sarcosine, N-methylisoleucine, 6-N-methyllysine, N-methylvaline, norvaline, norleucine, ornithine, and others too numerous to mention, that are listed in 63 *Fed. Reg.*, 29620, 29622, incorporated by reference herein.

D. Leaving or Activating Groups

Where mentioned with regard to the synthesis of the polymer conjugates described herein, suitable leaving groups or activating groups include, without limitations, moieties such as N-hydroxybenzotriazolyl, halogen, N-hydroxyphthalimidyl, p-nitrophenoxy, imidazolyl, N-hydroxysuccinimidyl; thiazolidinyl thione, or other good leaving groups as will be apparent to those of ordinary skill. For purposes of the present invention, leaving groups are to be understood as those groups which are capable of reacting with an amino group (nucleophile) found on the vancomycin compound.

E. Synthesis of Polymer Conjugates

Synthesis of specific representative polymer prodrugs is set forth in the Examples. Generally, however, in one preferred method of preparing a prodrug of the invention, the vancomycin-polymer conjugates are prepared by reacting a vancomycin compound such as, for example, a compound of formula (V) as shown above with a polymer residue i.e. a linear, terminally branched or multi-arm polymer residue, that contains at least one leaving group capable of reacting with the sugar ($V_3$) amino group of a vancomycin compound. This is done in the presence of at least about a 20-fold molar excess of triethylamine (TEA) and a sufficient amount of dimethylformamide (DMF). The ratio of vancomycin to the polymer residue is based on the amount of leaving groups present on the branched polymer. Preferably, there is at least about a 1:1 ratio of vancomycin to leaving groups.

Important aspects of this embodiment are the selection and amount of the base used in the reaction of the vancomycin compound with the activated polymer, e.g. the polymer residue containing the leaving group. Since the vancomycin compounds employed in the invention usually contain two amino groups, care must be taken during the reaction so as to avoid formation cross-linked conjugates and/or heterogeneous mixtures of vancomycin-polymer conjugates in which the polymer termini are attached at more than one of the sugar amino ($V_3$) and N-methyl amino ($X_1$). It has been surprisingly found that when the preferred amount of at least about 20 equivalents of TEA in combination with a sufficient amount of DMF in the presence of a sufficient amount of 4 Å molecular sieves is used, it is possible to obtain a substantially homogeneous reaction product of a polymer residue containing a vancomycin compound attached to each terminal end thereof via the vancomycin $V_3$ amino group. In preferred aspects of the method, at least about 10 equivalents of TEA are used in the reaction while in more preferred aspects, at least about 20 equivalents are used most preferably 40 equivalents of TEA are used.

For purposes of the present invention, the amount of the solvent DMF employed in the reaction is referred to as a "sufficient amount". As will be appreciated by those of ordinary skill, this amount will be sufficient to dissolve the reactants. In most aspects of the invention, the amount of DMF employed will range form about 10 mL/g to about 500 mL/g and preferably from about 100 mL/g to about 200 mL/g based upon the vancomycin compound used.

In another aspect of the invention there are provided higher payload, polymer-vancomycin conjugates in which the termini of the polymer residue are attached to the $X_1$ or N-methyl amino group of the vancomycin compound. Such compounds can be formed by capping the $V_3$ amino group of a vancomycin compound of formula (I) and thereafter reacting the $V_3$ capped vancomycin compound with an activated polymer containing at least one leaving group capable of reacting with the N-methyl-amino group of the vancomycin compound under conditions sufficient to form polymer conjugates containing vancomycin molecules linked to each terminal through the vancomycin N-methyl amino group.

Further, in certain aspects of the invention, a low molecular weight (e.g. less than about 10,000) releasable polymer residue, or small molecular weight protecting group is used to temporarily protect the sugar amino group ($V_3$) in order to prepare the selective polymer-vancomycin N-methyl amino ($X_1$) derivatives. These protecting groups can be removed once the $X_1$ amino group(s) has/have been derivatized. The protecting groups can be hydrolyzed either in vitro in a PBS or similar buffer followed by purification or in vivo based upon enzymatic degradation.

In yet another aspect of the invention, polymer-vancomycin conjugates-having a polymer residue attached on both the sugaramino and-the N-methyl amino of said vancomycin compound are prepared by the reaction of the $V_3$-linked vancomycin compound with a second activated polymer linker in the presence of at least about a 5 fold molar excess amount of dimethylaminopyridine (DMAP) and a sufficient amount of a solvent which contains a mixture of dichloromethane (DCM) and dimethylformamide (DMF). In preferred aspects, the amount of base is from about 2 to about 20 fold molar excess and in more preferred aspects, the amount of base is from about 5 to about 10 fold molar excess. The solvent mixture is preferably about equal parts dichloromethane and dimethylformamide although the ratio of solvents can range from about 3:1 to about 1:3.

This alternative method provides the artisan with a more direct path to providing vancomycin-compounds containing identical polymer residues attached to both the $V_3$ and $X_1$ amino groups.

The activated polymers which can be employed in this process are preferably selected from among the linear, terminally branched and multi-arm polymer residues such as those described herein above.

Preferably the substituents are reacted in an inert solvent such as dimethylformamide (DMF), methylene chloride (DCM), tetrahydrofuran (THF), acetonitrile ($CH_3CN$), chloroform ($CHCl_3$), or mixtures thereof. The reaction is preferably conducted at a temperature from 0° C. up to about 22° C. (room temperature).

Regardless of the route selected, some of the preferred compounds which result from the synthetic techniques described herein include:

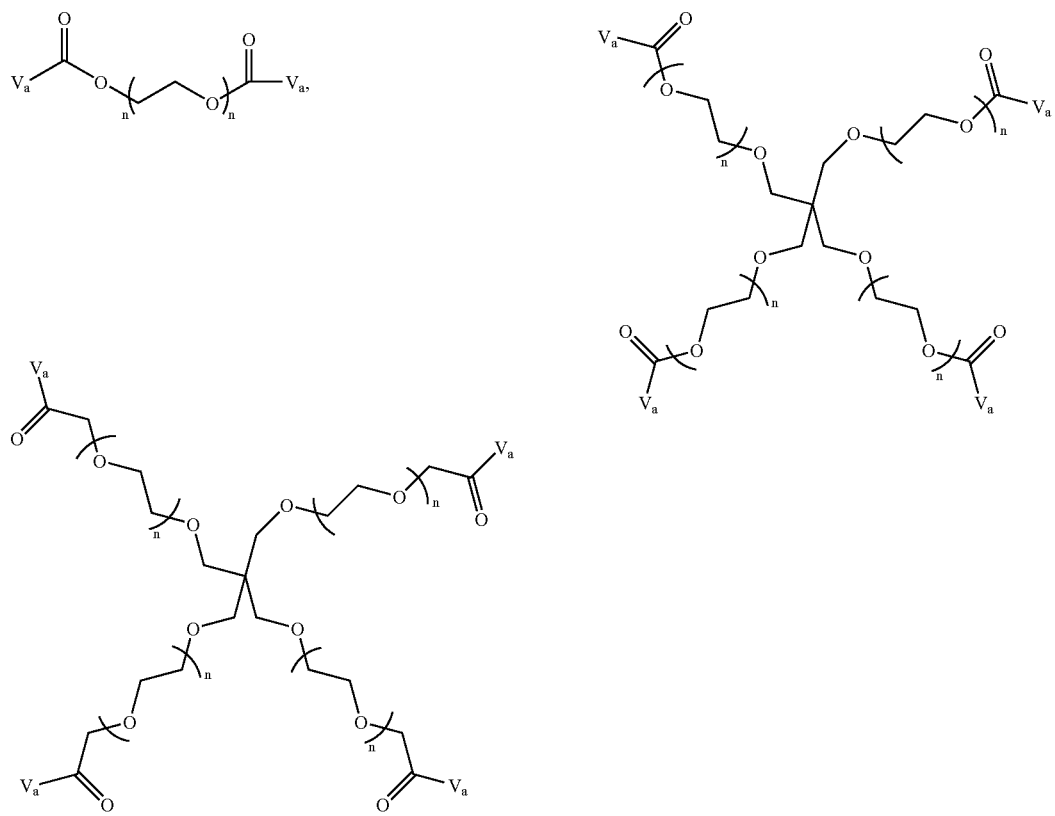

-continued
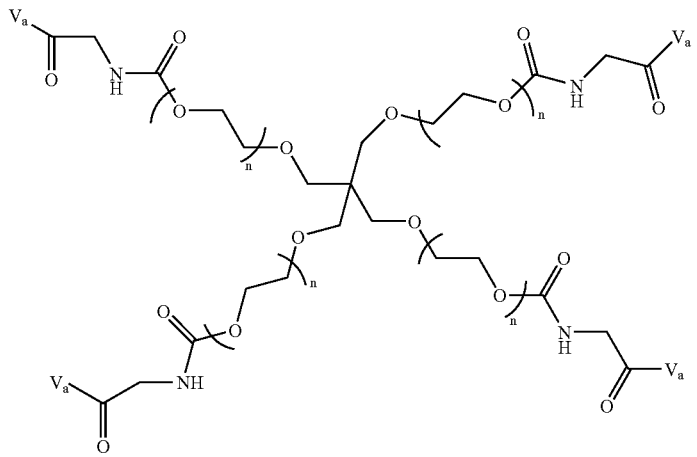
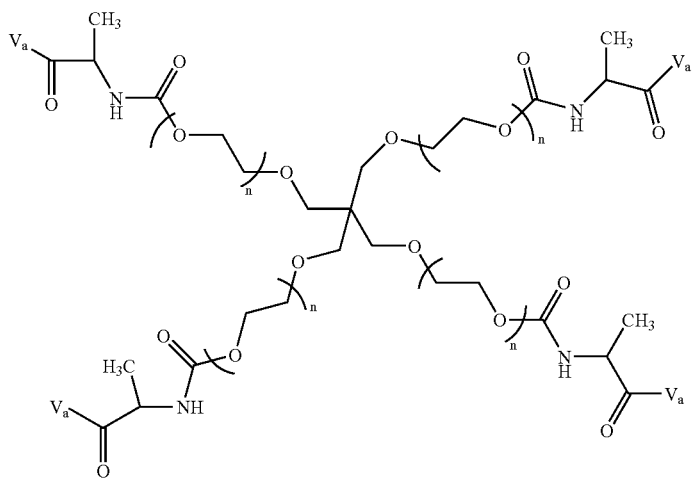
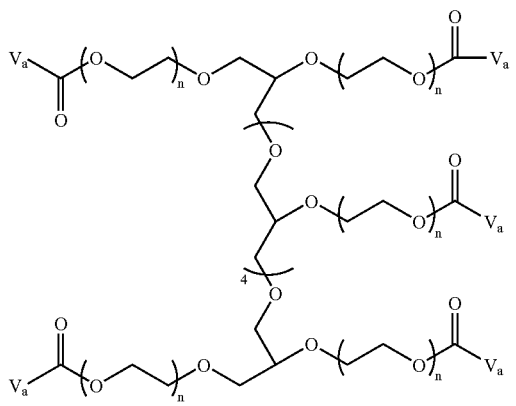
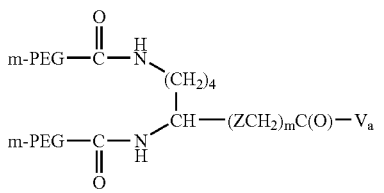
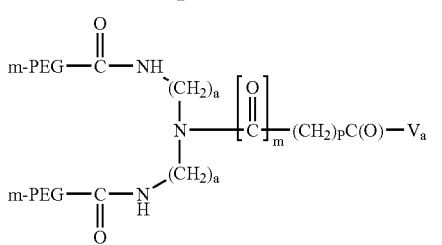
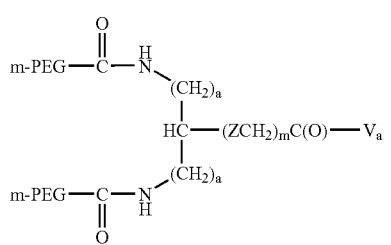

31
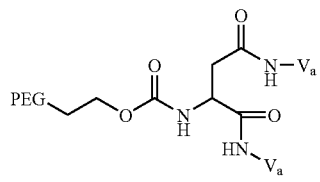
32
-continued
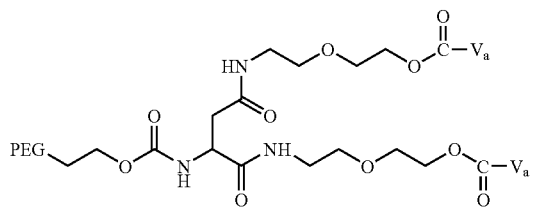
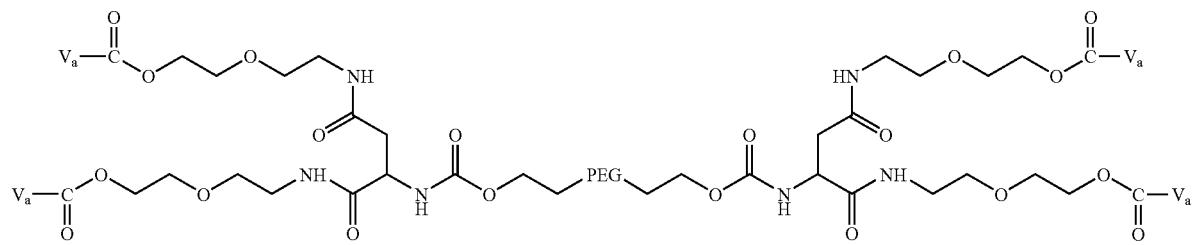
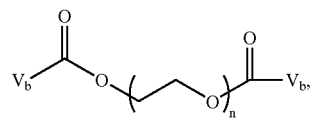
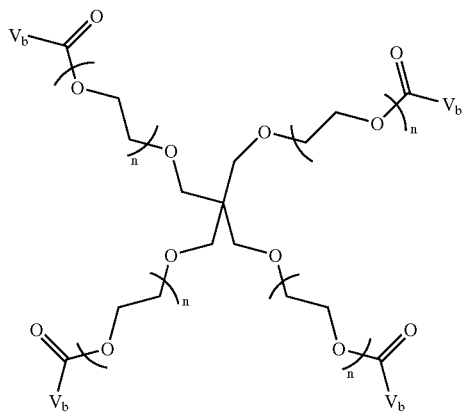
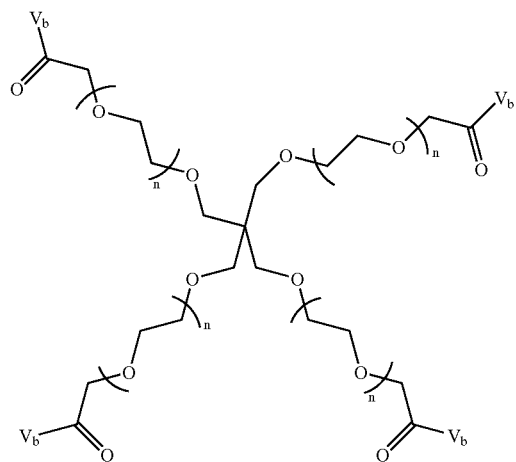

-continued
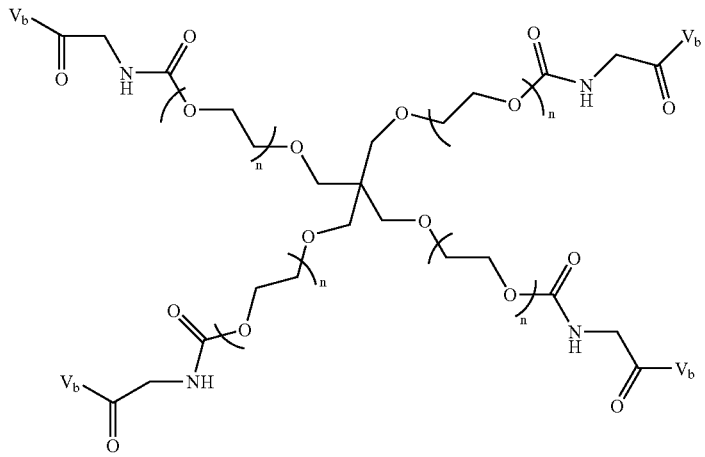
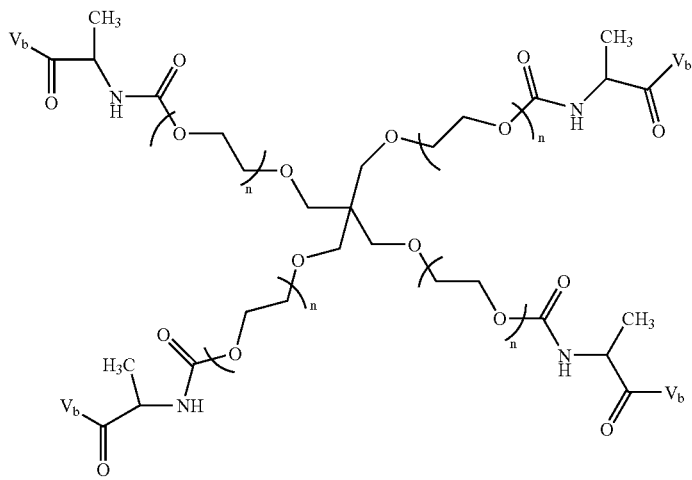
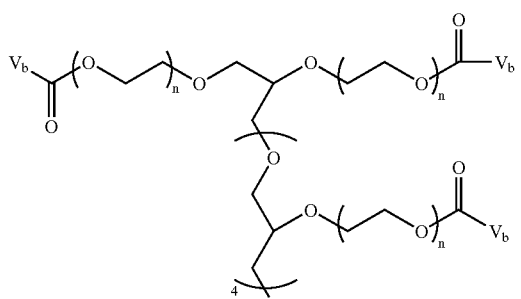
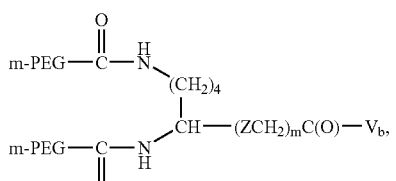
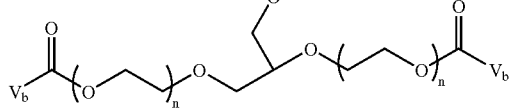
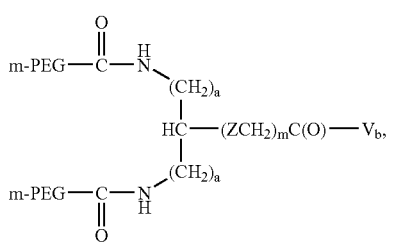

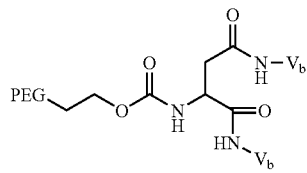
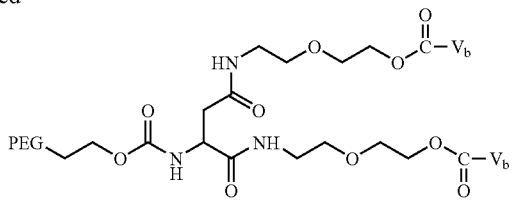
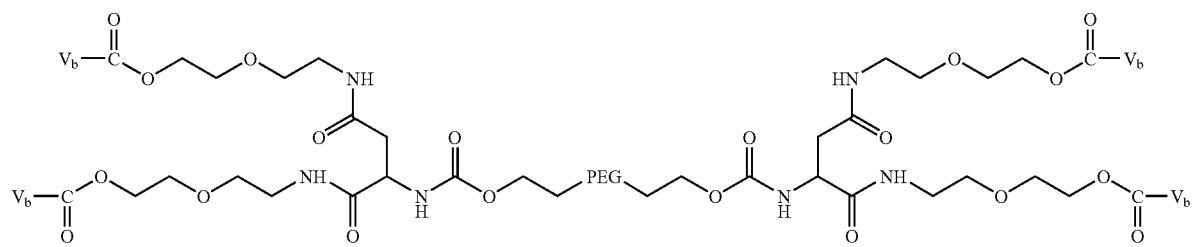
wherein:
PEG is
(a) is an integer of from about 1 to about 5;
Z is O, NR$_8$, S, SO or SO$_2$; where R$_8$ is H, C$_{1-8}$ alkyl, C$_{1-8}$ branched alkyl, C$_{1-8}$ substituted alkyl, aryl or aralkyl;
(m) is 0 or 1;
(p) is a positive integer, preferably from about 1 to about 6;
x is 10 to 2,300;
Va is
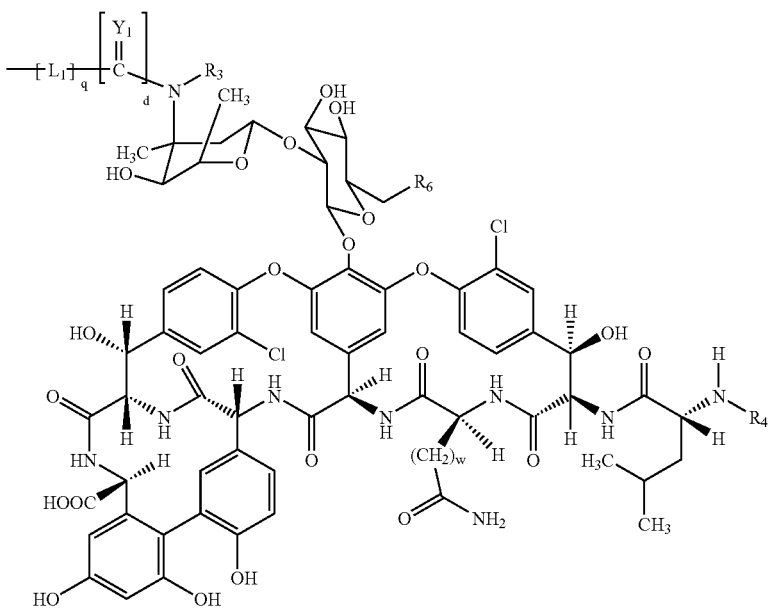
and Vb is:

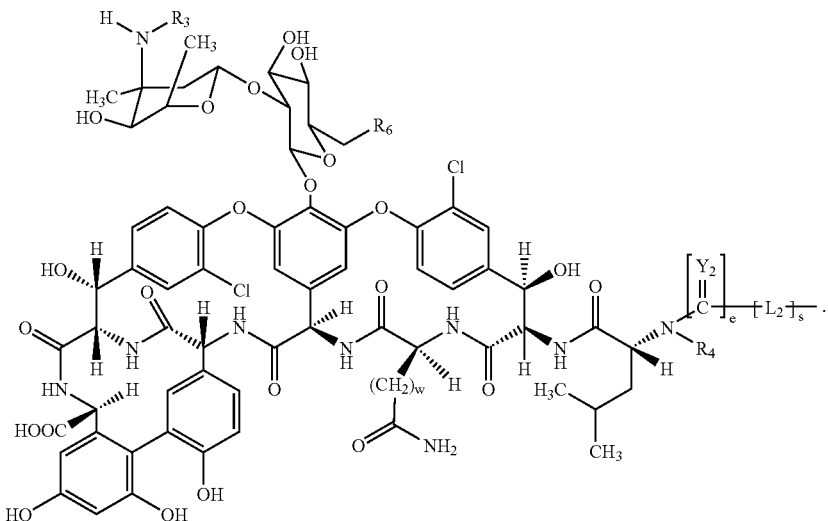

wherein, d, e, q, and S are each independently 0 or 1, and all other variables are as described above.

E. Methods of Treatment

Another aspect of the present invention provides methods of treatment for various vancomycin-sensitive infections in mammals. The methods include administering to the mammal in need of such treatment, an effective amount of the prodrug, i.e. vancomycin, which has been prepared as described herein.

The amount of the prodrug administered will depend upon the vancomycin compound selected. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, however, the vancomycin prodrugs are administered in amounts ranging from about 0.5 to about 60 mg/kg twice a week. Preferably, vancomycin is administered in amounts ranging from about 0.5 to about 30 mg/kg per day. The range set forth above is illustrative and those skilled in the art will determine the optimal dosing of the prodrug selected based on clinical experience and the treatment indication. Actual dosages will be apparent to the artisan without undue experimentation.

The prodrugs of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are parenterally administered to mammals in need thereof.

Another aspect of the invention is a method of treating vancomycin susceptible diseases in mammals using a combination of a vancomycin in unmodified or commonly available forms, e.g. vancomycin HCl, or other pharmaceutically acceptable salt, solvate or hydrate thereof, and a polymeric conjugate of the invention. The total amount of vancomycin administered to the patient in need thereof is an effective amount as mentioned above, based on the amount of vancomycin. The combination of prodrug and vancomycin derivative can be administered to a patient in need of the drug or such treatment as part of a single pharmaceutical dosage form (e.g. intravenous or parenteral injection/infusion or oral dosage form) or as part of a treatment regimen in which both of the vancomycin and vancomycin prodrug are administered as separate dosage forms to a patient in need thereof. Thus, the vancomycin and polymeric conjugate of the invention are administered either substantially concurrently in separate dosage forms or combined in a unit dosage form.

Since the present invention can relate to treatment with a combination of vancomycin dosage forms which can be administered separately, the invention also relates to combining separate pharmaceutical compositions in kit form. That is, a kit is contemplated wherein two separate unit dosage forms are combined: for example a vancomycin pharmaceutical composition and a separate pharmaceutical composition containing a polymer conjugate of the invention. The kit will preferably include directions for the administration of the separate components. The kit form is particularly advantageous when the separate components must be administered in different dosage forms and/or are administered at different dosage intervals. Thus a kit may comprise, in separate containers in a single package, pharmaceutical compositions for use in a therapeutically effective amount of vancomycin or a pharmaceutically acceptable salt, solvate or hydrate thereof in a pharmaceutically acceptable carrier and in a second container a therapeutically effective amount of a polymer conjugate as described herein in the form of a pharmaceutically acceptable salt, solvate or hydrate thereof in a pharmaceutically acceptable carrier.

EXAMPLES

Figure 2:
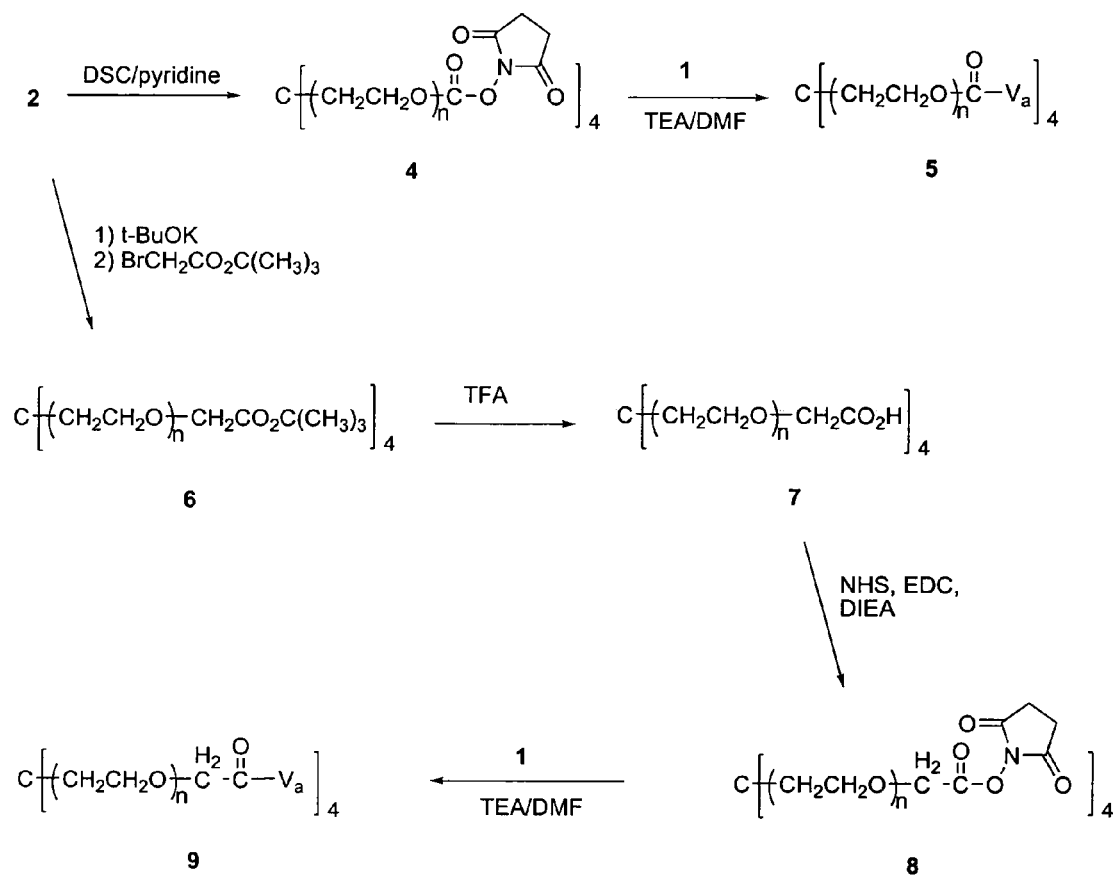
Figure 3:
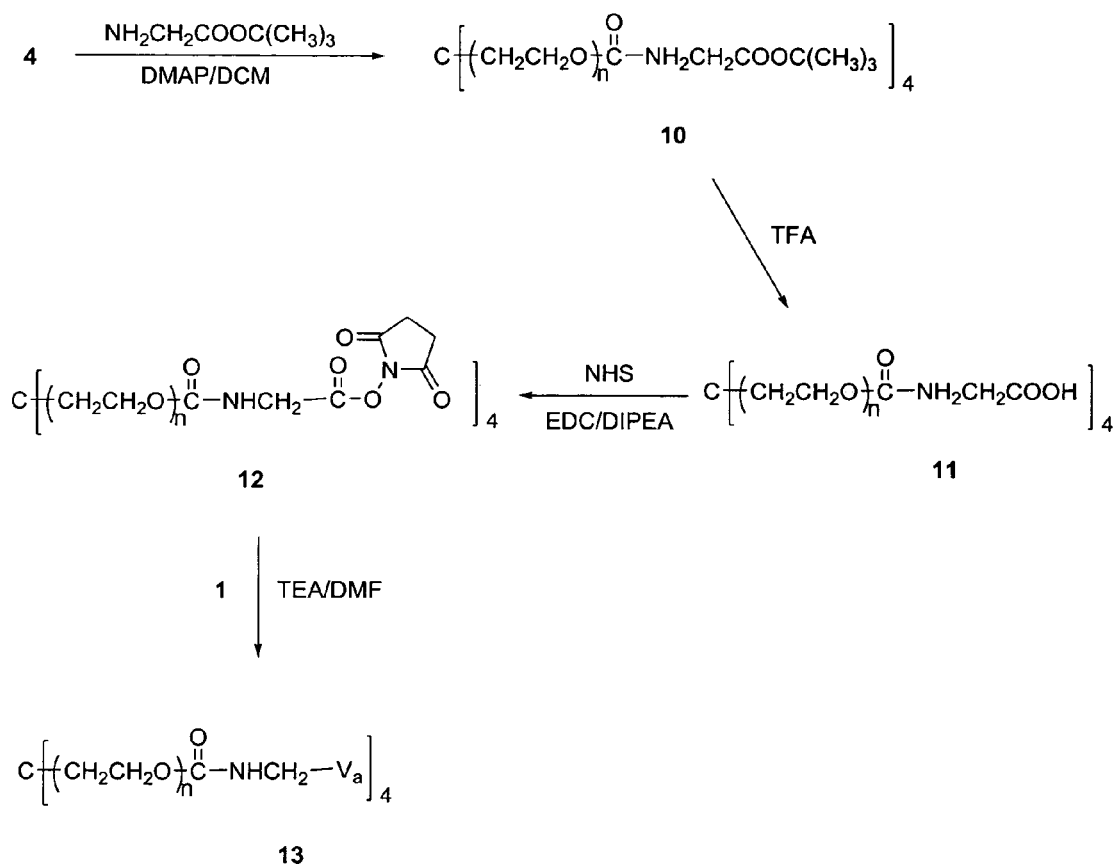
Figure 4:
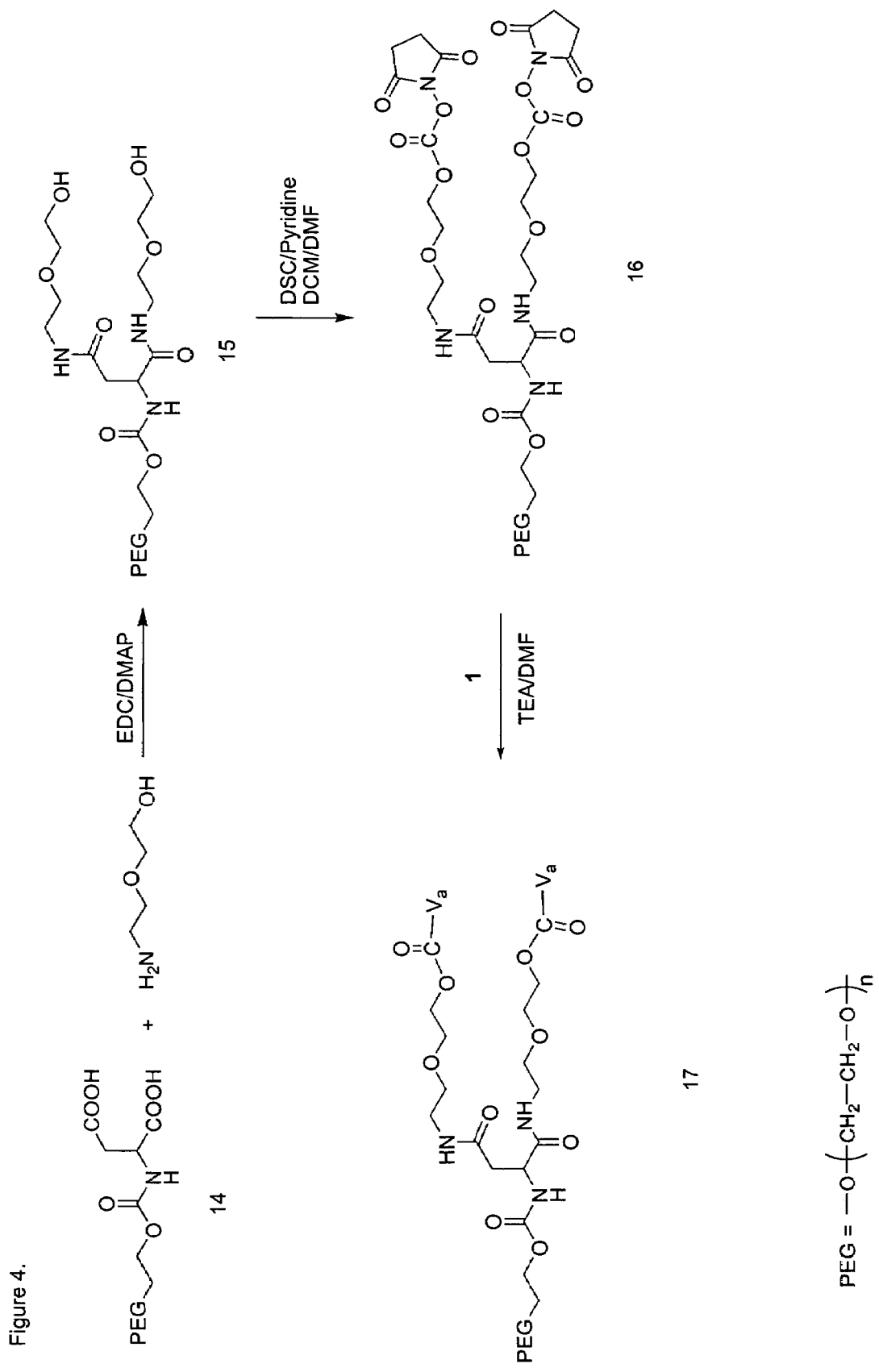
Figure 5:
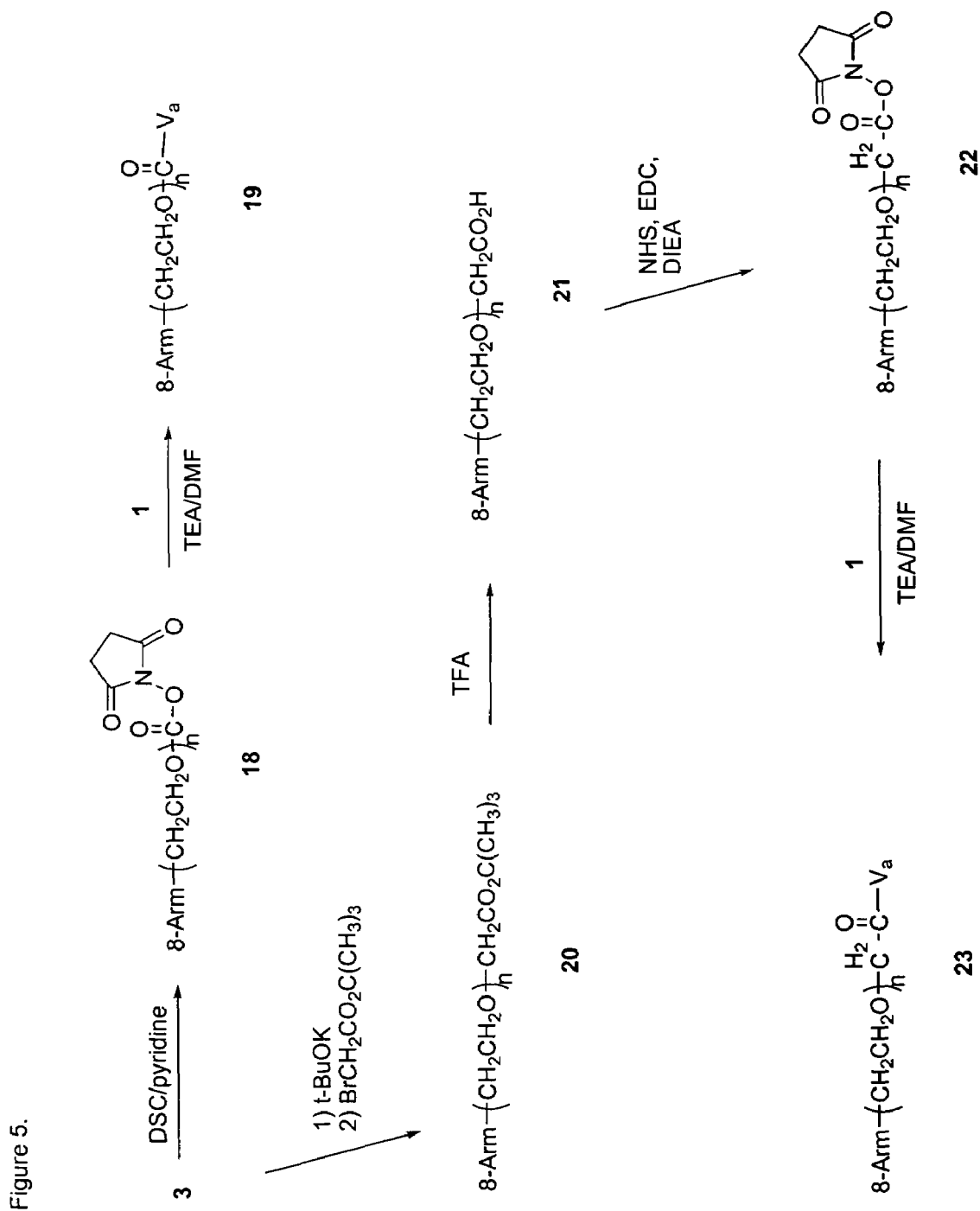

The following examples serve to provide further appreciation of the invention but are not meant in any way to restrict the effective scope of the invention. The underlined and bold-faced numbers recited below correspond to those shown in FIGS. 1-5.

General Procedures

All reactions were run under an atmosphere of dry nitrogen or argon. Commercial reagents were used without further purification. All PEG compounds were dried under vacuum or by azeotropic distillation from toluene prior to use. $^{13}$C NMR spectra were obtained at 75.46 MHz using a Varian Mercury® 300 NMR spectrometer and deuterated chloroform and pyridine as the solvents unless otherwise specified. Chemical shifts (δ) are reported in parts per million (ppm) downfield from tetramethylsilane (TMS). All vancomycin-polymer conjugation reactions were carried out in the presence of 4 Angstrom molecular sieves.

HPLC Method

The reaction mixtures and the purity of intermediates and final products were monitored by a Beckman Coulter System Gold® HPLC instrument. It employs a ZOBAX® 300SB C8 reversed phase column (150×4.6 mm) or a Phenomenex Jupiter® 300A C18 reversed phase column (150×4.6 mm) with a multiwavelength UV detector, using a gradient of 10-90% of acetonitrile in 0.05% trifluoroacetic acid (TFA) at a flow rate of 1 mL/min.

Example 1

Compound 4

A solution of 2 (mw 40 kDa, 23 g, 0.575 mmol) and disuccinimidyl carbonate (DSC, 2.36 g, 9.2 mmol) in methylene chloride (DCM, 230 mL) and dimethylformamide (DMF, 23 mL) was cooled to 0° C., followed by the addition of pyridine (0.75 mL, 9.2 mmol). This mixture was allowed to warm to room temperature overnight, followed by filtration through Celite® and partial removal of the solvent from the filtrate by rotary evaporation under reduced pressure. The crude product was precipitated with ether and collected by filtration, and crystallized from 20% DMF/isopropanol (IPA) to yield 4 (20.1 g, 0.496 mmol, 86%). $^{13}$C NMR (67.8 MHz, $C_5D_5N$) δ 168.2, 151.1, 70.7-69.6 (PEG), 68.0, 45.2, 25.2.

Example 2

Compound 5

To a solution of 1 (0.550 g, 0.37 mmol) and triethylamine (TEA, 2.06 mL, 14.8 mmol) in DMF (50 mL) was added 4 (3 g, 0.074 mmol) and 5.5 g molecular sieves (4 Å) and the mixture stirred at 30 ° C. for 5 hrs. The reaction mixture was filtered through celite, the PEG conjugate precipitated with ether, filtered, and crystallized from DMF/ethanol (50:50) three times to give 5 (2.0 g, 0.0436 mmol, 59%).

Example 3

Compound 6

A solution of 2 (10 g, 0.025 mmol) in toluene (150 mL) was azeotroped for 2 hrs with the removal of 50 mL of distillate. The reaction mixture was then cooled to 30 ° C., followed by the addition of a 1.0 M solution potassium t-butoxide in t-butanol (1.7 ml, 1.7 mmol). The resulting mixture was stirred for 1 hr at 45° C., cooled to 30° C., followed by the addition of t-butyl bromoacetate (0.4 g, 2.0 mmol). The resulting mixture was refluxed for 18 hrs, followed by filtration through Celite and partial removal of the solvent from the filtrate by rotary evaporation under reduced pressure. The crude product was precipitated with ether, collected by filtration, and crystallized from IPA to yield 6 (8.1 g, 0.20 mmol, 80%). $^{13}$C NMR (67.8 MHz, $C_5D_5N$) δ 169.1, 81.1, 72.2-69.6 (PEG), 68.7, 45.2, 27.9.

Example 4

Compound 7

A solution of 6 (10.6 g, 0.26 mmol) in DCM (100 mL) and trifluoroacetic acid (TFA, 50 mL) was stirred for 7 hrs at room temperature, followed by partial removal of DCM by evaporation under reduced pressure. The product was precipitated with ethyl ether, filtered, and washed with ether to yield 7 (9.3 g, 0.0178 mmol, 89%). $^{13}$C NMR (67.8 MHz, $C_5D_5N$) δ 170.9, 72.2-69.6 (PEG), 68.2, 45.2.

Example 5

Compound 8

A solution of 7 (11 g, 0.273 mmol), N-hydroxysuccinimide (NHS, 0.25 g, 2.19 mmol), and diisopropylethyl amine (DIEA, 1.1 mL, 6.56 mmol) in DCM (88 mL) and DMF (22 mL) was cooled to 0° C., followed by the addition of 1-(3-dimethylaminopropyl)-3-ethylcarbodiimide hydrochloride (EDC, 0.63 g, 3.28 mmol). This mixture was allowed to warm to room temperature overnight, followed by filtration through Celite® and partial removal of the solvent from the filtrate under reduced pressure. The crude product was precipitated with ether, collected by filtration and crystallized from 20% DMF/IPA to yield 8 (10.4 g, 0.257 mmol, 94%). $^{13}$C NMR (67.8 MHz, $C_5D_5N$) δ 168.3, 165.5, 72.2-68.3 (PEG), 66.2, 45.2, 25.3.

Example 6

Compound 9

To a solution of 1 (0.66 g, 0.44 mmol) and TEA (2.47 mL, 17.77 mmol) in DMF (60 mL) was added 8 (3 g, 0.074 mmol) and 6.6 g molecular sieves (4 Å), and the resulting mixture stirred at 30° C. for 12 hrs. The reaction mixture was filtered through celite, the PEG conjugate precipitated with ether, and finally crystallized from DMF/ethanol (50:50) three times to give 9 (2.4 g, 0.0522 mmol, 71%).

Example 7

Compound 10

A solution of 4 (6.86 g, 0.169 mmol) and glycine t-butylester (0.227 g, 1.36 mmol) in DCM (70 mL) was cooled to 0° C., followed by the addition of DMAP (0.165 g, 1.36 mmol).

The mixture was allowed to warm to room temperature overnight, followed by filtration and partial removal of the solvent from the filtrate by rotary evaporator under reduced pressure. The crude product was precipitated with ether, collected by filtration, and crystallized from IPA to yield 10 (6.11 g, 0.150 mmol, 89%). $^{13}$C NMR (67.8 MHz, $C_5D_5N$) δ 168.7, 156.0, 81.3, 72.19-70.3 (PEG), 69.2, 63.9, 45.3, 43.1, 27.9.

Example 8

Compound 11

A solution of 10 (6 g, 0.147 mmol) in DCM (60 mL) and TFA (30 mL) was stirred for 4 hrs at room temperature, followed by partial removal of the solvents under reduced pressure. The product was precipitated with ethyl ether, filtered, and washed with ether to yield 11 (5 g, 0.122 mmol, 83%). $^{13}$C NMR (67.8 MHz, $C_5D_5N$) δ 170.5 ,156.0, 72.21-69.9 (PEG), 69.2, 63.8, 45.3, 42.2.

Example 9

Compound 12

A solution of 11 (2.5 g, 0.0619 mmol) and NHS (0.0569 g, 0.495 mmol) in DCM (20 mL) and DMF (5 mL) was cooled to 0° C., followed by the addition of EDC (0.143 g, 0.743 mmol) and DIEA (0.26 mL, 1.485 mmol). This mixture was allowed to warm to room temperature overnight, followed by filtration and partial removal of the solvent from the filtrate by evaporation in vacuo. The crude product was precipitated with ether, filtered, and crystallized from 20% DMF/IPA to give 12 (2.1 g, 0.0520 mmol, 84%). $^{13}$C NMR (67.8 MHz, $C_5D_5N$) δ 168.5, 165.9, 156.1, 72.21-70.3 (PEG), 69.9, 64.2, 45.3, 40.3, 25.4.

Example 10

Compound 13

To a solution of 1 (0.466 g, 0.314 mmol) and TEA (1.75 mL, 12.5 mmol) in DMF (50 mL) was added (12) 8 (2.54 g, 0.0627 mmol) and 5 g molecular sieves (4 Å). The mixture was stirred at 25-30° C. overnight, followed by filtration and precipitation with ether. The crude product was crystallized from DMF/ethanol (1:1) to yield 13 (1.4 g, 0.0303 mmol, 48%).

Example 11

Compound 15

A solution of 14 (10 g, 0.248 mmol) and aminoethoxy ethanol (0.5 mL, 4.96 mmol) in DCM (200 mL) was cooled to 0° C., followed by the addition of EDC (0.952 g, 4.96 mmol) and DMAP (0.605 g, 4.96 mmol). The reaction mixture was allowed to warm to room temperature overnight, followed by filtration and partial removal of the solvent by evaporation in vacuo. The crude product was precipitated with ether, filtered, and crystallized from IPA to yield 15 (8.92 g, 0.219 mmol, 88% yield). $^{13}$C NMR (67.8 MHz, $C_5D_5N$) δ 170.9, 170.6, 155.8, 70.3-68.8 (PEG), 64.1, 61.3, 51.5, 39.3, 38.0.

Example 12

Compound 16

A solution of 15 (5 g, 0.121 mmol) and DSC (0.494 g, 1.93 mmol) in DCM (50 mL) and DMF (5 mL) was cooled to 0° C., followed by the addition of pyridine (0.16 mL, 1.928 mmol). The mixture was allowed to warm to room temperature overnight, followed by filtration and partial removal of the solvent by evaporation under reduced pressure. The crude product was precipitated with ether, filtered, and crystallized from IPA to yielded 16 (4.2 g, 0.097 mmol, 80%). $^{13}$CNMR (67.8 MHz, $C_5D_5N$) δ 171.0, 170.6, 169.1, 156.0, 151.6, 71.6-70.0 (PEG), 68.3, 64.4, 51.9, 39.5, 38.1, 25.7.

Example 13

Compound 17

To a solution of 1 (0.465 g, 0.313 mmol) and TEA (1.75 mL, 12.51 mmol) in DMF (50 mL) was added 16 (2.58 g, 0.0625 mmol) and 7 g molecular sieves (4 Å), and the resulting mixture stirred at 25-30° C. overnight, followed by filtration. The crude product was precipitated with ether, filtered, and crystallized from DMF/ethanol (1:1) to give 17 (2.1 g, 0.045 mmol, 72.1%).

Example 14

Compound 18

A solution of 3 (mw 20 kDa, 25 g, 1.25 mmol) and DSC (10.2 g, 40.0 mmol) in methylene chloride (DCM, 250 mL) and dimethylforamide (DMF 25 mL) was cooled to 0° C., followed by the addition of pyridine (3.20 mL, 40.0 mmol). This mixture was allowed to warm to room temperature overnight, followed by filtration through Celite and partial removal of the solvent from the filtrate by rotary evaporation under reduced pressure. The crude product was precipitated out with ether and collected by filtration, crystallized from 20% DMF/EPA to yield 18 (23.4 g, 1.11 mmol, 89%). $^{13}$C NMR (67.8 MHz, $C_5D_5N$) δ 168.2, 151.2, 70.5-69.5 (PEG), 68.0, 25.2.

Example 15

Compound 19

To a solution of 1 (2.53 g, 1.70 mmol) and TEA (14.2 mL, 102 mmol) in DMF (200 mL) was added 18 (3 g, 0.142 mmol) and 5.5 g molecular sieves (4 Å) and the mixture stirred at 30° C. for 12 hrs. The reaction mixture was filtered through celite, the PEG conjugate precipitated with ether and purified by column chromatograph using gel filtration column (superdex75 or sephadex G75) to give 19 (1.4 g, 0.044 mmol, 59%) after lipholization. (Note: the product can also be purified by dialysis using a membrane with a molecular weight cut-off of 12000-14000.)

Example 16

Compound 20

A solution of 3 (30 g, 1.50 mmol) in toluene (350 mL) was azeotroped for 2 hrs with the removal of 50 mL of distillate. The reaction mixture was then cooled to 30° C., followed by the addition of a 1.0 molar solution potassium t-butoxide in t-butanol (24 ml, 24 mmol). The resulting mixture was stirred for 1 hr at 45° C., cooled to 30° C., followed by the addition of t-butyl bromoacetate (9.4 g, 48.2 mmol). The resulting mixture was refluxed for 18 hrs, filtered through Celite and the solvent was concentrated under reduced pressure. The crude product was precipitated with ether and collected by filtration, then crystallized from IPA to yield 20 (26.2 g, 1.25 mmol, 83%). $^{13}$C NMR (67.8 MHz, $C_5D_5N$) δ 169.1, 81.1, 70.6-69.5 (PEG), 68.7, 27.9.

Example 17
Compound 21

A solution of 20 (13.0 g, 0.62 mmol) in DCM (130 mL) and TFA (65 mL) was stirred for 7 hrs at room temperature, followed by partial removal of DCM by evaporation under reduced pressure. The product was precipitated with ethyl ether, filtered, and washed with ether to yield 21 (12.4 g, 0.61 mmol, 98%). $^{13}$C NMR (67.8 MHz, $C_5D_5N$) δ 171.1, 71.3-69.5 (PEG), 68.3.

Example 18
Compound 22

A solution of 21 (1.5 g, 0.073 mmol), NHS (0.14 g, 1.2 mmol), and DIEA (0.41 mL, 2.34 mmol) in DCM (12 mL) and DMF (3 mL) was cooled to 0° C., followed by the addition of EDC (0.34 g, 1.76 mmol). This mixture was allowed to warm to room temperature overnight, followed by filtration through Celite and partial removal of the solvent from the filtrate under reduced pressure. The product was precipitated with ether, collected by filtration, and crystallized from 20% DMF/IPA to yield 22 (1.2 g, 0.055 mmol, 75%). $^{13}$C NMR (67.8 MHz, $C_5D_5N$) δ 168.4, 165.6, 71.0-69.5 (PEG), 25.4.

Example 19
Compound 23

To a solution of 1 (0.825 g, 0.55 mmol) and TEA (3.09 mL, 22.2 mmol) in DMF (60 mL) is added 22 (1.2 g, 0.055 mmol) and 6.6 g molecular sieves (4 Å) and the mixture stirred at 30° C. for 12 hrs. The reaction mixture is filtered through celite, the PEG conjugate precipitated with ether, and purified by column chromatograph using a gel filtration column (superdex75 or sephadex G75) to give 23 (1.05 g, 0.033 mmol, 60%) after lipholization. (Note: this product can also be purified by dialysis using a membrane with a molecular weight cut-off of 12000-14000.)

Other embodiments of the invention will be apparent to one skilled in the art from a consideration of this specification or practice of the invention disclosed herein. It is intended that the specification and examples be considered as exemplary only, with the true scope and spirit of the invention being indicated by the following claims.

We claim:

1. A compound of the formula

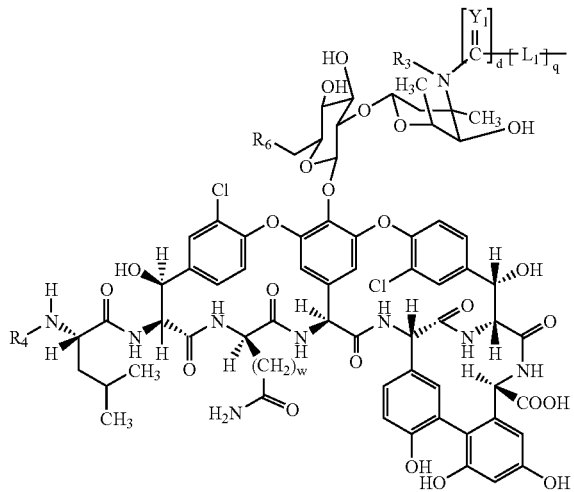

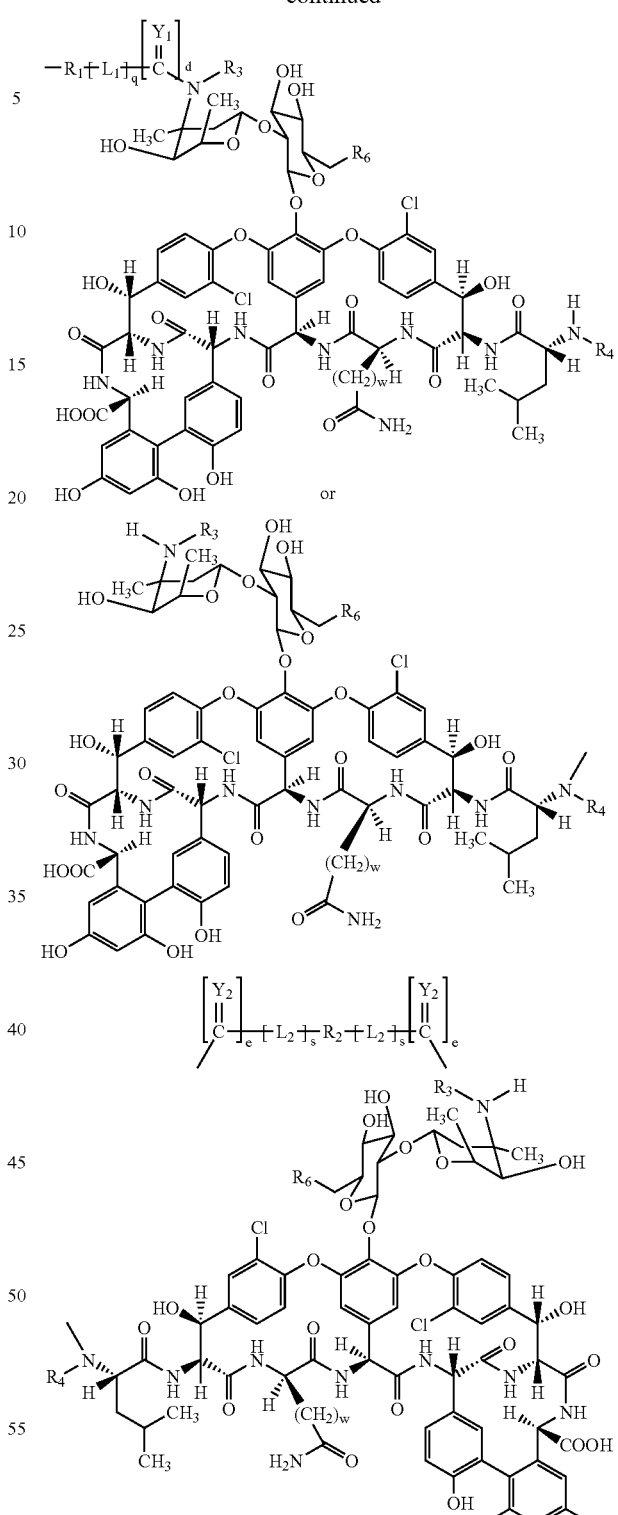

wherein:

$R_3$-$R_5$ are each independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ alkenyls, $C_{3-12}$ branched alkenyls, $C_{1-6}$ alkynyls, $C_{3-12}$ branched alkynyls, $C_{1-6}$ heteroalkyls, substituted $C_{1-6}$ hetero-alkyls, $C_{1-6}$ alkoxyalkyl, phenoxyalkyl and $C_{1-6}$ heteroalkoxys;

$R_6$ is OH, NH-aryl, NH-aralkyl, or NH—$C_{1-12}$ alkyl, w is 1 or 2;

$R_1$ is a polyalkylene oxide;

$Y_1$ is O, S or $NR_5$;

q is 0, 1 or 2;

d is 0 or 1;

$R_2$ is a polyalkylene oxide;

$Y_2$ is O, S or $NR_5$;

s is 0, 1 or 2;

e is 0 or 1; and $L_{1-2}$ are independently selected from the group consisting of amino acids and —[C(O)]$_v$NR$_{25}$(CR$_{26}$R$_{27}$)$_t$—,
—[C(O)]$_v$(CR$_{26}$R$_{27}$)$_t$—,
—[C(O)]$_v$NR$_{25}$(CR$_{26}$R$_{27}$O)$_t$—,
—[C(O)]$_v$NR$_{25}$(CR$_{26}$R$_{27}$O)$_t$(CR$_{28}$R$_{29}$)$_y$O—,
—[C(O)]$_v$NR$_{25}$(CR$_{26}$R$_{27}$O)$_t$(CR$_{28}$R$_{29}$)$_y$—,
—[C(O)]$_v$NR$_{25}$(CR$_{26}$R$_{27}$)$_t$O—,
—[C(O)]$_v$NR$_{25}$(CR$_{26}$R$_{27}$O)$_t$(CR$_{28}$R$_{29}$O)$_y$NR$_{30}$—,
—[C(O)]$_v$O(CR$_{26}$R$_{27}$)$_t$NR$_{30}$—,
—[C(O)]$_v$O(CR$_{26}$R$_{27}$)$_t$O—,
—[C(O)]$_v$NR$_{25}$(CR$_{26}$R$_{27}$)$_t$NR$_{30}$—,
—[C(O)]$_v$NR$_{25}$(CR$_{26}$R$_{27}$)$_t$(CR$_{28}$CR$_{29}$O)$_y$—,
—[C(O)]$_v$NR$_{25}$(CR$_{26}$CR$_{27}$O)$_t$(CR$_{28}$R$_{29}$)$_y$NR$_{30}$—,
—[C(O)]$_v$O(CR$_{26}$CR$_{27}$O)$_t$NR$_{30}$—,

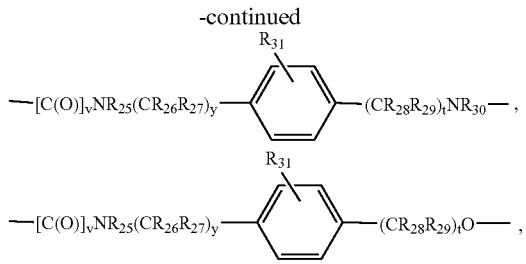

wherein:

$R_{25}$-$R_{30}$ are independently selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxyalkyl, phenoxyalkyl and $C_{1-6}$ heteroalkoxys;

$R_{31}$ is selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxyalkyl, phenoxyalkyl and $C_{1-6}$ heteroalkoxys, $NO_2$, haloalkyl and halogen;

t and y are individually selected positive integers ranging from about 1 to about 4; and v is 0 or 1.

2. A compound of claim 1 of the formula:

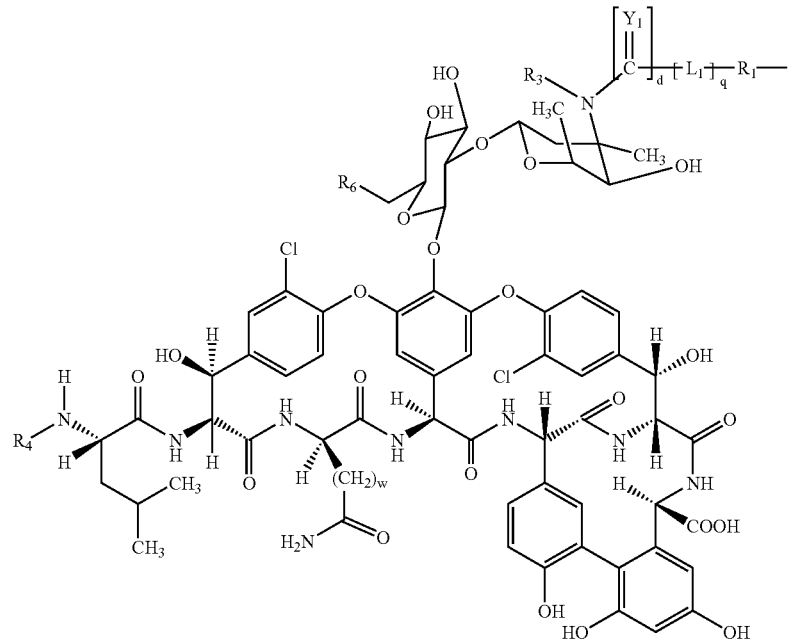

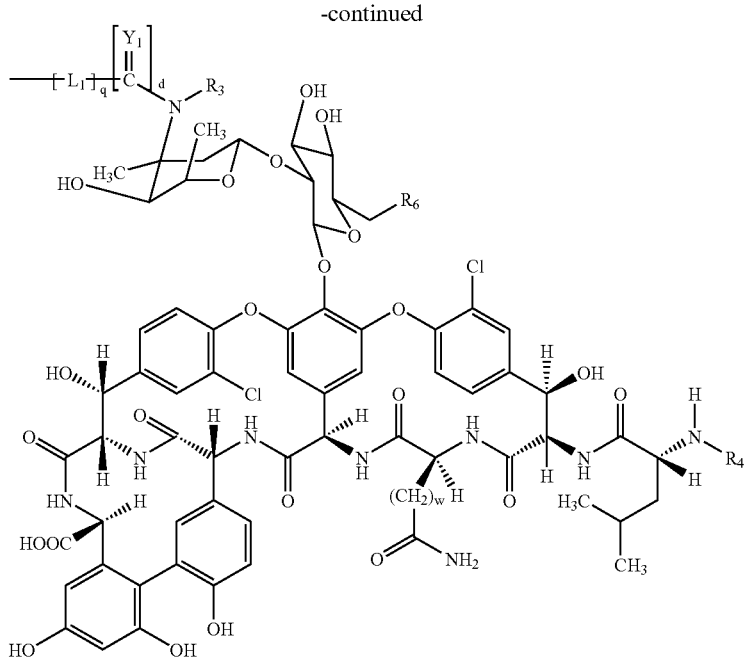
wherein:
$Y_1$ is O;
$R_3$ and $R_4$ are each independently hydrogen or $CH_3$;
$R_6$ is OH or NH-aryl;
q is 0-2; and
w is 1.
3. A compound of claim 1 of the formula:
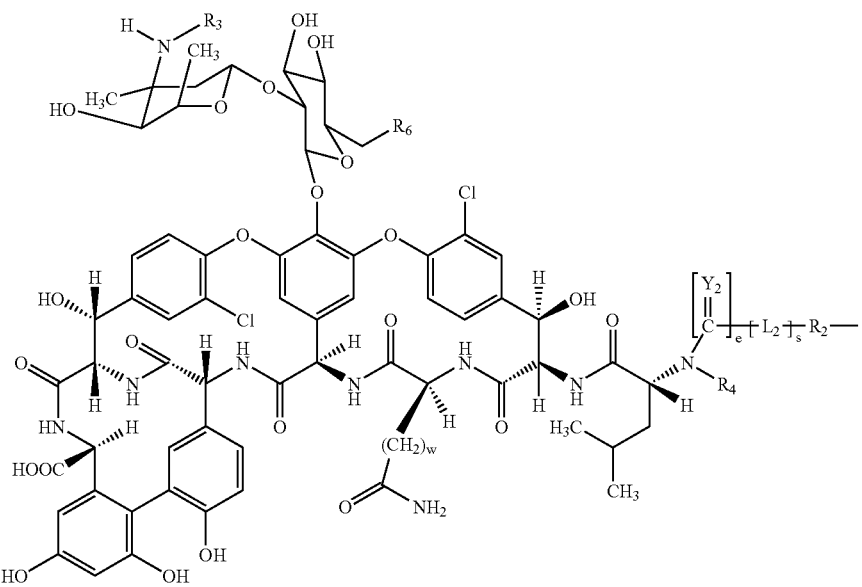

-continued

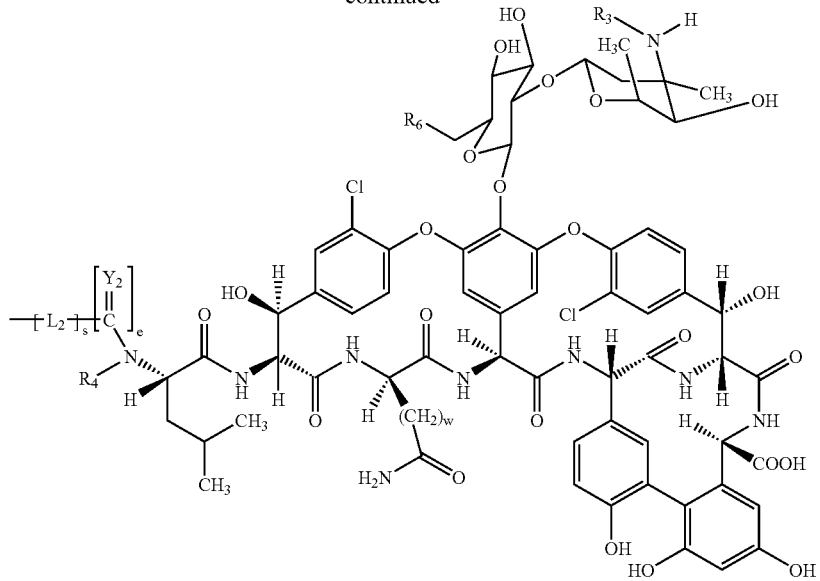

wherein:
$Y_2$ is O;
$R_3$ and $R_4$ are each independently hydrogen or $CH_3$;
$R_6$ is OH or NH-aryl;
s is 0-2; and
w is 1.

4. The compound of claim 1 wherein:
$Y_1$ and $Y_2$ are independently O;
$R_3$ and $R_4$ are each independently hydrogen or $CH_3$;
$R_6$ is OH or NH-aryl;
q and s are independently 0-2; and
w is 1.

5. The compound of claim 1 wherein the amino acid is selected from the group consisting of alanine, valine, leucine, isoleucine, glycine, serine, threonine, methionine, cysteine, phenylalanine, tyrosine, tryptophan, aspartic acid, glutamic acid, lysine, arginine, histidine and proline.

6. The compound of claim 1, wherein said polyalkylene oxide comprises polyethylene glycol.

7. The compound of claim 1, wherein said linear polyalkylene oxide is selected from the group consisting of:

O—$(CH_2CH_2O)_x$—,

—O—$C(O)CH_2$—O—$(CH_2CH_2O)_x$—$CH_2C(O)$—O—,

—$NR_7CH_2CH_2$—O—$(CH_2CH_2O)_x$—$CH_2CH_2NR_7$—, and

—$SHCH_2CH_2$—O—$(CH_2CH_2O)_x$—$CH_2CH_2SH$—, wherein
$R_7$ is selected from that which defines $R_3$, and
x is an integer of from about 10 to about 2,300.

8. The compound of claim 1, wherein said polyalkylene oxide has a total number average molecular weight of from about 5,000 to about 100,000 daltons.

9. The compound of claim 1, wherein said polyalkylene oxide has a total number average molecular weight of from about 10,000 to about 80,000 daltons.

10. The compound of claim 1, wherein said polyalkylene oxide has a total number average molecular weight of from about 20,000 to about 40,000 daltons.

11. A compound of the formula, selected from the group consisting of:

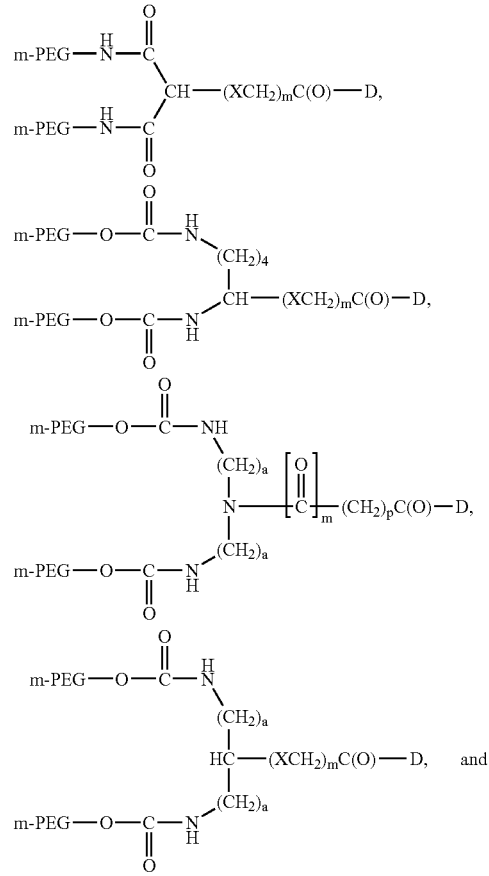

-continued
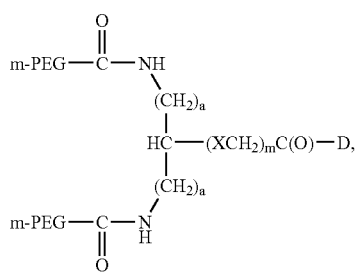
wherein
(a) is an integer of from about 1 to about 5;
X is O, $NR_8$, S, SO or $SO_2$; where $R_8$ is H, $C_{1-8}$ alkyl, $C_{1-8}$ branched alkyl, $C_{1-8}$ substituted alkyl, aryl or aralkyl;
(m) is 0 or 1;
(p) is a positive integer of from about 1 to about 6;
D is $V_a$ or $V_b$, wherein
$V_a$ is
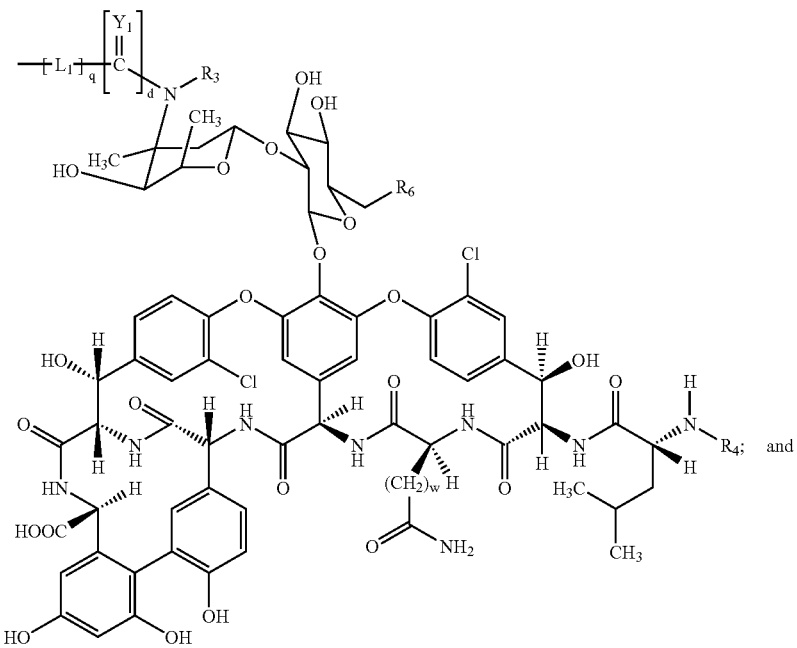
$V_b$ is a moiety of the formula:
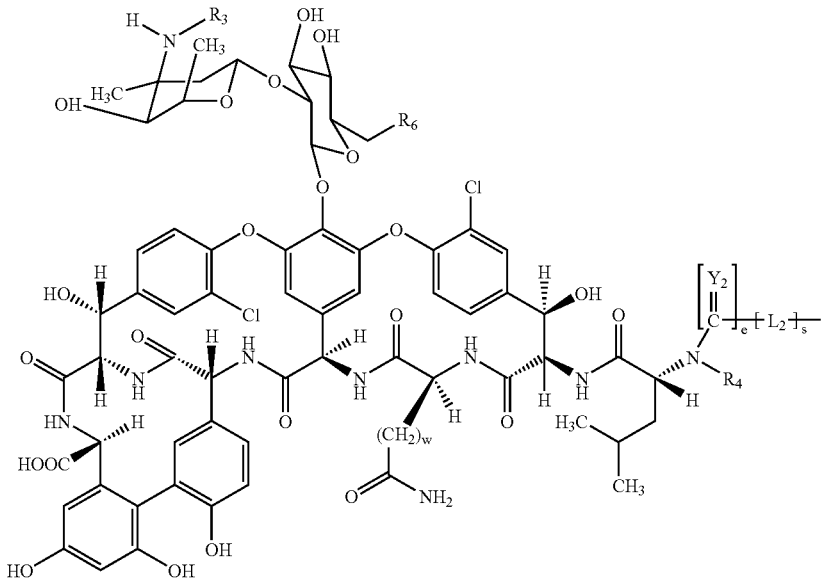

wherein $R_3$-$R_5$ are each independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ alkenyls, $C_{3-12}$ branched alkenyls, $C_{1-6}$ alkynyls, $C_{3-12}$ branched alkynyls, $C_{1-6}$ heteroalkyls, substituted $C_{1-6}$ hetero-alkyls, $C_{1-6}$ alkoxyalkyl, phenoxyalkyl and $C_{1-6}$ heteroalkoxys;

$R_6$ is OH, NH-aryl, NH-aralkyl, or NH—$C_{1-12}$ alkyl, w is 1 or 2;

$Y_1$ is O, S or $NR_5$;

q is 0, 1 or 2;

d is 0 or 1;

$Y_2$ is O, S or $NR_5$;

s is 0, 1 or 2;

e is 0 or 1; and $L_{1-2}$ are independently selected from the group consisting of amino acids and —[C(O)]$_v$NR$_{25}$(CR$_{26}$R$_{27}$)$_t$—,
—[C(O)]$_v$(CR$_{26}$R$_{27}$)$_t$—,
—[C(O)]$_v$NR$_{25}$(CR$_{26}$R$_{27}$O)$_t$—,
—[C(O)]$_v$NR$_{25}$(CR$_{26}$R$_{27}$O)$_t$(CR$_{28}$R$_{29}$)$_y$O—,
—[C(O)]$_v$NR$_{25}$(CR$_{26}$R$_{27}$O)$_t$(CR$_{28}$R$_{29}$)$_y$—,
—[C(O)]$_v$NR$_{25}$(CR$_{26}$R$_{27}$)$_t$O—,
—[C(O)]$_v$NR$_{25}$(CR$_{26}$R$_{27}$)$_t$(CR$_{28}$R$_{29}$O)$_y$NR$_{30}$—,
—[C(O)]$_v$O(CR$_{26}$R$_{27}$)$_t$NR$_{30}$—,
—[C(O)]$_v$O(CR$_{26}$R$_{27}$)$_t$O—,
—[C(O)]$_v$NR$_{25}$(CR$_{26}$R$_{27}$)$_t$NR$_{30}$—,
—[C(O)]$_v$NR$_{25}$(CR$_{26}$R$_{27}$)$_t$(CR$_{28}$R$_{29}$O)$_y$—,
—[C(O)]$_v$NR$_{25}$(CR$_{26}$R$_{27}$O)$_t$(CR$_{28}$R$_{29}$)$_y$NR$_{30}$—,
—[C(O)]$_v$O(CR$_{26}$R$_{27}$O)$_t$NR$_{30}$—,

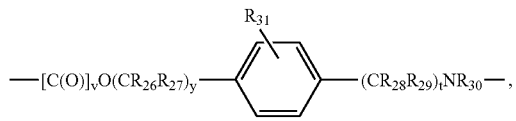

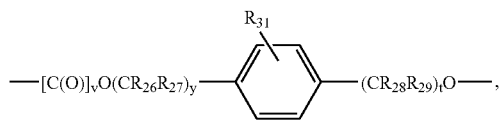

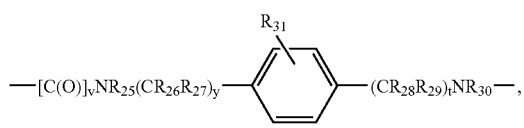

and

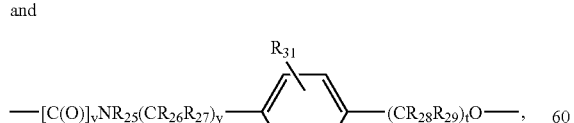

wherein:

$R_{25}$-$R_{30}$ are independently selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxyalkyl, phenoxyalkyl and $C_{1-6}$ heteroalkoxys;

$R_{31}$ is selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxyalkyl, phenoxyalkyl and $C_{1-6}$ heteroalkoxys, $NO_2$, haloalkyl and halogen;

t and y are individually selected positive integers ranging from about 1 to about 4; and v is 0 or 1;

mPEG is

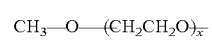

wherein x is an integer from about 10 to about 2,300, and has a number average molecular weight of from about 2,000 to about 100,000 daltons.

12. The compound of claim 11, wherein mPEG has a number average molecular weight of from about 20,000 to about 40,000 daltons.

13. A compound of the formula, selected from the group consisting of:

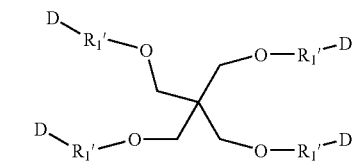

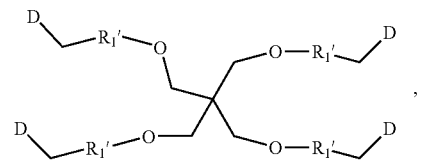

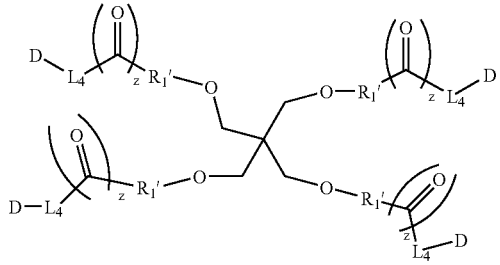

and

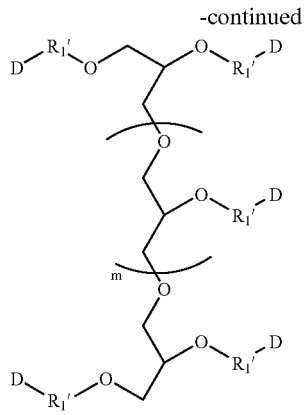
wherein,
m is 0-4;
z is 0 or 1;
$L_4$ is the same as that which defines $L_{1-2}$;
D is $V_a$ or $V_b$;
$R_1'$ is
—$(CH_2CH_2O)_x$—,
—$(CH_2CH_2O)_x$—$CH_2C(O)$—,
—$(CH_2CH_2O)_x$—$CH_2CH_2NR_7$— or
—$(CH_2CH_2O)_x$—$CH_2CH_2SH$—,
wherein
x is an integer of from about 10 to about 2,300;
$R_7$ is selected from that which defines $R_3$;
$V_a$ is
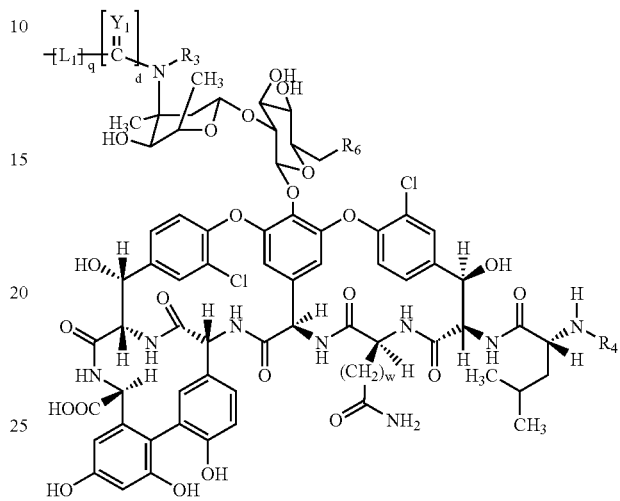
; and
$V_b$ is
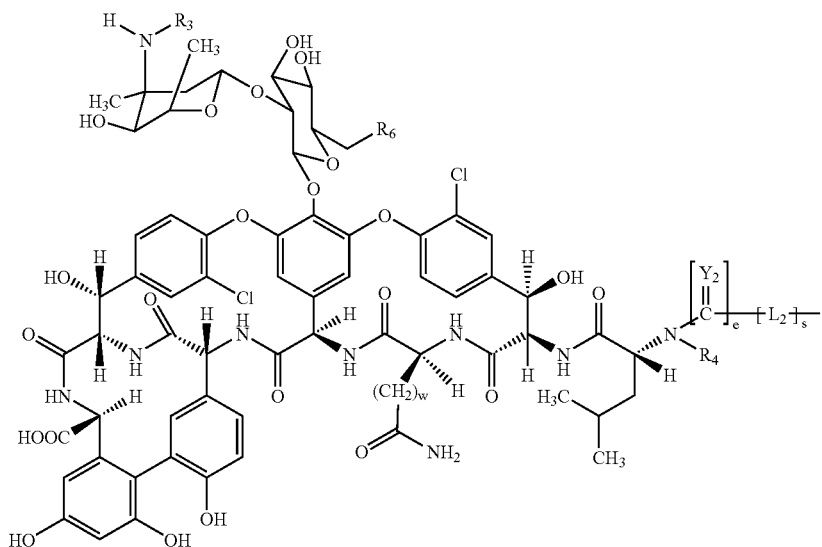

wherein

R$_3$-R$_5$ are each independently selected from among hydrogen, C$_{1-6}$ alkyls, C$_{3-12}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ alkenyls, C$_{3-12}$ branched alkenyls, C$_{1-6}$ alkynyls, C$_{3-12}$ branched alkynyls, C$_{1-6}$ heteroalkyls, substituted C$_{1-6}$ hetero-alkyls, C$_{1-6}$ alkoxyalkyl, phenoxyalkyl and C$_{1-6}$ heteroalkoxys;

R$_6$ is OH, NH-aryl, NH-aralkyl, or NH—C$_{1-12}$ alkyl, w is 1 or 2;

Y$_1$ is O, S or NR$_5$;

q is 0, 1 or 2;

d is 0 or 1; and

Y$_2$ is O, S or NR$_5$;

s is 0, 1 or 2;

e is 0 or 1; and

L$_{1-2}$ are independently selected from the group consisting of amino acids and —[C(O)]$_v$NR$_{25}$(CR$_{26}$R$_{27}$)$_t$—,
—[C(O)]$_v$(CR$_{26}$R$_{27}$)$_t$—,
—[C(O)]$_v$NR$_{25}$(CR$_{26}$R$_{27}$O)$_t$—,
—[C(O)]$_v$NR$_{25}$(CR$_{26}$R$_{27}$O)$_t$(CR$_{28}$R$_{29}$)$_y$O—,
—[C(O)]$_v$NR$_{25}$(CR$_{26}$R$_{27}$O)$_t$(CR$_{28}$R$_{29}$)$_y$—,
—[C(O)]$_v$NR$_{25}$(CR$_{26}$R$_{27}$)$_t$O—,
—[C(O)]$_v$NR$_{25}$(CR$_{26}$R$_{27}$)$_t$(CR$_{28}$R$_{29}$O)$_y$NR$_{30}$—,
—[C(O)]$_v$O(CR$_{26}$R$_{27}$)$_t$NR$_{30}$—,
—[C(O)]$_v$O(CR$_{26}$R$_{27}$)$_t$O—,
—[C(O)]$_v$NR$_{25}$(CR$_{26}$R$_{27}$)$_t$NR$_{30}$—,
—[C(O)]$_v$NR$_{25}$(CR$_{26}$R$_{27}$)$_t$(CR$_{28}$R$_{29}$O)$_y$—,
—[C(O)]$_v$NR$_{25}$(CR$_{26}$R$_{27}$O)$_t$(CR$_{28}$R$_{29}$)$_y$NR$_{30}$—,
—[C(O)]$_v$O(CR$_{26}$CR$_{27}$O)$_t$NR$_{30}$—, —[C(O)]$_v$O(CR$_{26}$R$_{27}$)$_y$—[C$_6$H$_3$(R$_{31}$)]—(CR$_{28}$R$_{29}$)$_t$NR$_{30}$—, —[C(O)]$_v$O(CR$_{26}$R$_{27}$)$_y$—[C$_6$H$_3$(R$_{31}$)]—(CR$_{28}$R$_{29}$)$_t$O—, -continued —[C(O)]$_v$NR$_{25}$(CR$_{26}$R$_{27}$)$_y$—[C$_6$H$_3$(R$_{31}$)]—(CR$_{28}$R$_{29}$)$_t$NR$_{30}$—, and —[C(O)]$_v$NR$_{25}$(CR$_{26}$R$_{27}$)$_y$—[C$_6$H$_3$(R$_{31}$)]—(CR$_{28}$R$_{29}$)$_t$O—, wherein:

R$_{25}$-R$_{30}$ are independently selected from the group consisting of hydrogen, C$_{1-6}$ alkyls, C$_{2-6}$ alkenyls, C$_{2-6}$ alkynyls, C$_{3-19}$ branched alkyls, C$_{3-8}$ cycloalkyls, C$_{1-6}$ substituted alkyls, C$_{2-6}$ substituted alkenyls, C$_{2-6}$ substituted alkynyls, C$_{3-8}$ substituted cycloalkyls, aryls, substituted aryls, aralkyls, C$_{1-6}$ heteroalkyls, substituted C$_{1-6}$ hetero-alkyls, C$_{1-6}$ alkoxyalkyl, phenoxyalkyl and C$_{1-6}$ heteroalkoxys;

R$_{31}$ is selected from the group consisting of hydrogen, C$_{1-6}$ alkyls, C$_{2-6}$ alkenyls, C$_{2-6}$ alkynyls, C$_{3-19}$ branched alkyls, C$_{3-8}$ cycloalkyls, C$_{1-6}$ substituted alkyls, C$_{2-6}$ substituted alkenyls, C$_{2-6}$ substituted alkynyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxylkyl, phenoxyalkyl and C$_{1-6}$ heteroalkoxys, NO$_2$, haloalkyl and halogen;

t and y are individually selected positive integers ranging from about 1 to about 4; and v is 0 or 1.

14. The compound of claim 13, wherein x is a positive integer such that the polymeric portion has a number average molecular weight of from about 2,000 to about 100,000 daltons.

15. The compound of claim 13, wherein x is a positive integer such that the polymeric portion has a number average molecular weight of from about 20,000 to about 40,000 daltons.

16. A compound selected from the group consisting of:

-continued
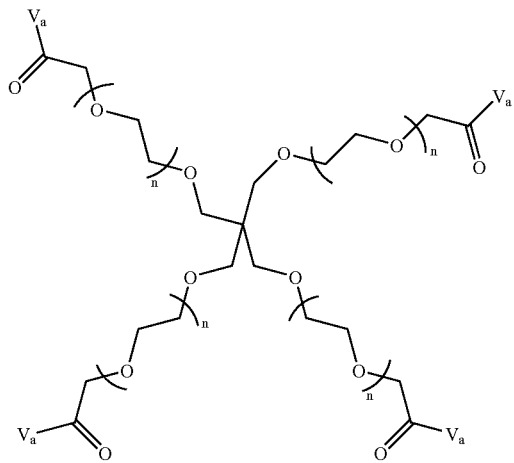
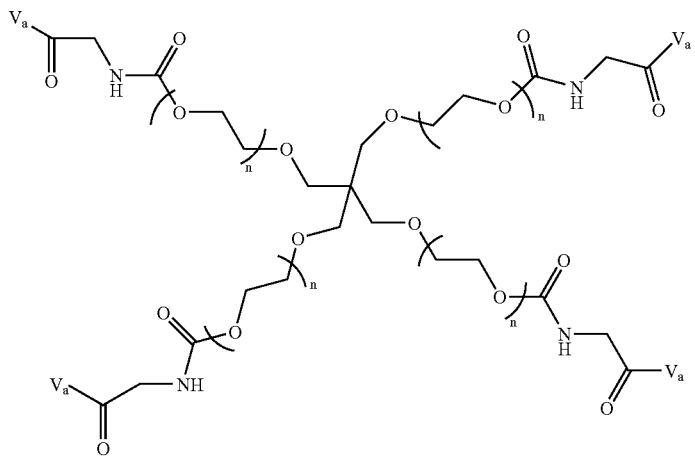
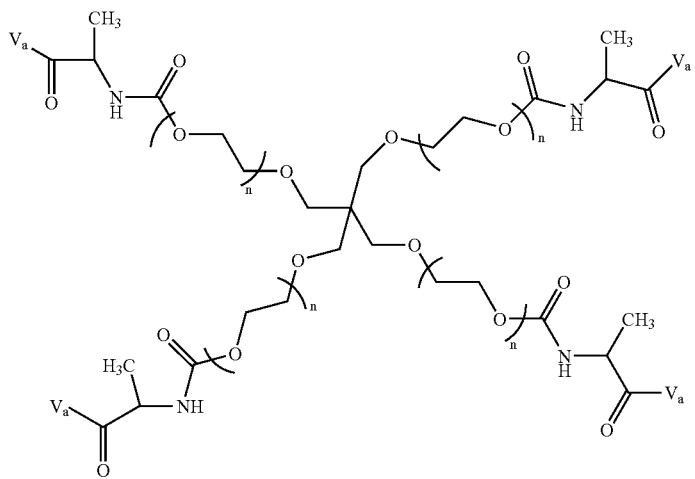

-continued
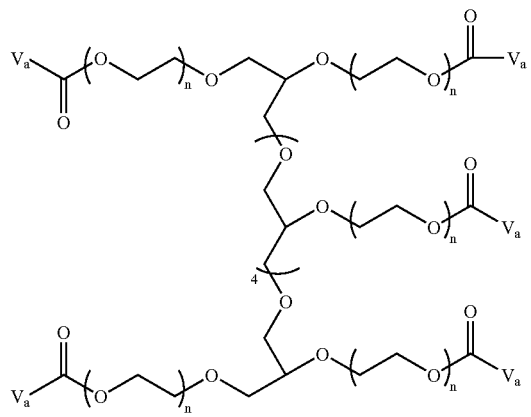
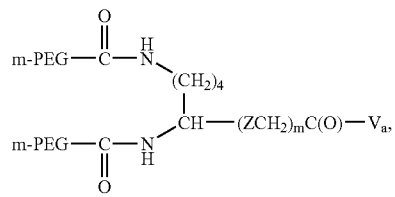
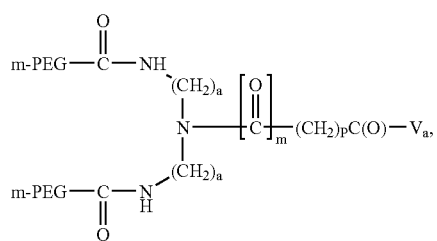
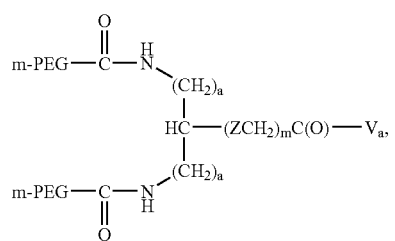
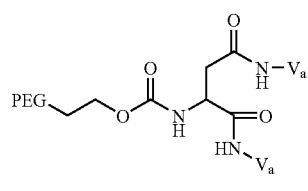
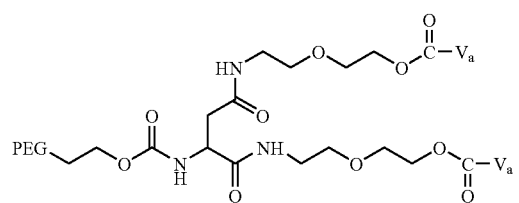
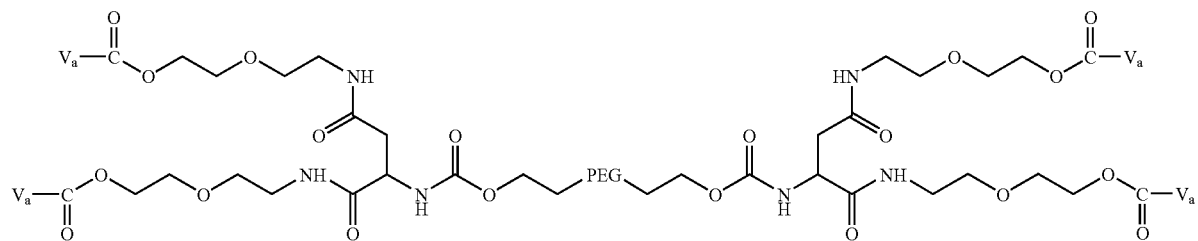

wherein:

mPEG is

(a) is an integer of from about 1 to about 5;

Z is O, $NR_8$, S, SO or $SO_2$, where $R_8$ is H, $C_{1-8}$ alkyl, $C_{1-8}$ branched alkyl, $C_{1-8}$ substituted alkyl, aryl or aralkyl;

(m) is 0 or 1;
(p) is a positive integer of from about 1 to about 6;
x is an integer of from about 10 to about 2,300; and
$V_a$ is

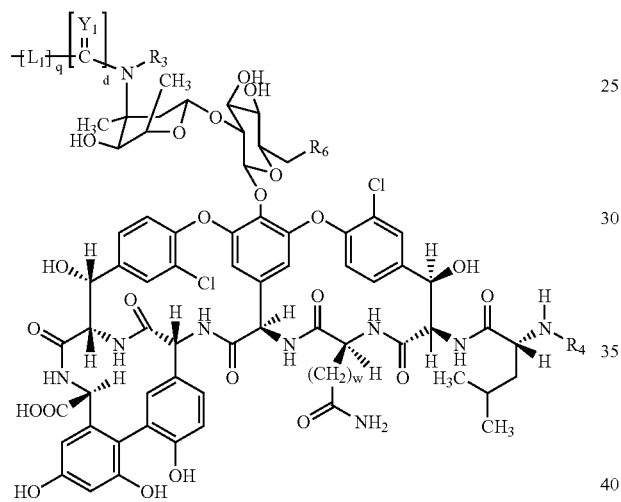

wherein:

$Y_1$ is O;

$L_1$ is selected from the group consisting of amino acids and

—[C(O)]$_v$NR$_{25}$(CR$_{26}$R$_{27}$)$_t$—,
—[C(O)]$_v$(CR$_{26}$R$_{27}$)$_t$—,
—[C(O)]$_v$NR$_{25}$(CR$_{26}$R$_{27}$O)$_t$—,
—[C(O)]$_v$NR$_{25}$(CR$_{26}$R$_{27}$O)$_t$(CR$_{28}$R$_{29}$)$_y$O—,
—[C(O)]$_v$NR$_{25}$(CR$_{26}$R$_{27}$O)$_t$(CR$_{28}$R$_{29}$)$_y$—,
—[C(O)]$_v$NR$_{25}$(CR$_{26}$R$_{27}$)$_t$O—,
—[C(O)]$_v$NR$_{25}$(CR$_{26}$R$_{27}$)$_t$(CR$_{28}$R$_{29}$O)$_y$NR$_{30}$—,
—[C(O)]$_v$O(CR$_{26}$R$_{27}$)$_t$NR$_{30}$—,
—[C(O)]$_v$O(CR$_{26}$R$_{27}$)$_t$O—,
—[C(O)]$_v$NR$_{25}$(CR$_{26}$R$_{27}$)$_t$NR$_{30}$—,
—[C(O)]$_v$NR$_{25}$(CR$_{26}$R$_{27}$)$_t$(CR$_{28}$R$_{29}$O)$_y$—,
—[C(O)]$_v$NR$_{25}$(CR$_{26}$R$_{27}$O)$_t$(CR$_{28}$R$_{29}$)$_y$NR$_{30}$—,

——[C(O)]$_v$O(CR$_{26}$CR$_{27}$O)$_t$NR$_{30}$—,

-continued

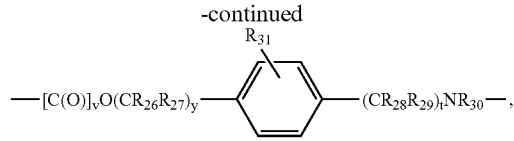

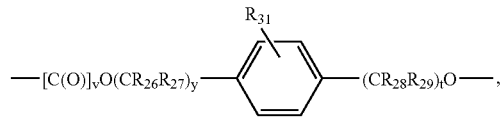

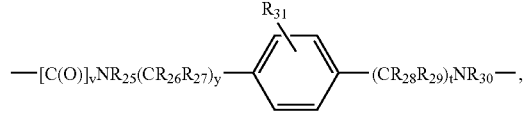

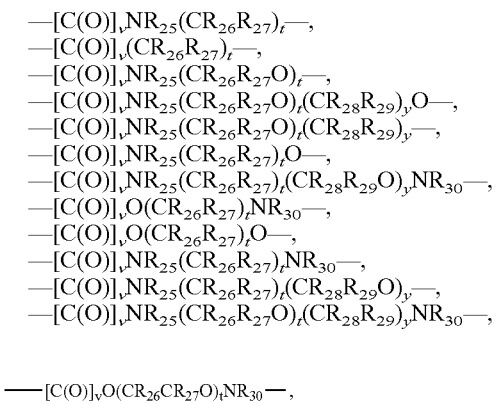

wherein:
R$_{25}$-R$_{30}$ are independently selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls,
$C_{1-6}$ substituted alkyls, $C_{2-6}$ substituted alkenyls, $C_{2-6}$ substituted alkynyls,
$C_{3-8}$ substituted cycloalkyls, aryls, substituted aryls, aralkyls, $C_{1-6}$ heteroalkyls, substituted $C_{1-6}$heteroalkyls, $C_{1-6}$alkoxyalkyl, phenoxyalkyl and $C_{1-6}$ heteroalkoxys;
R$_{31}$ is selected from the group consisting of hydrogen, $C_{1-6}$alkyls,
$C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted
$C_{1-6}$ heteroalkyls, $C_{1-6}$ alkoxyalkyl, phenoxyalkyl and $C_{1-6}$ heteroalkoxys,
$NO_2$, haloalkyl and halogen;
t and y are individually selected positive integers ranging from about 1 to about 4, and
v is 0 or 1;
$R_3$ and $R_4$ are each independently hydrogen or $CH_3$;
$R_6$ is OH or NH-aryl;
q is 0-2;
d is 0 or 1; and
w is 1.

17. A compound selected from the group consisting of:
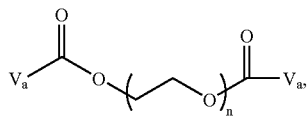
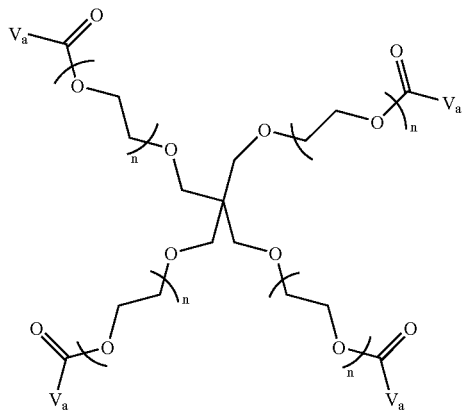
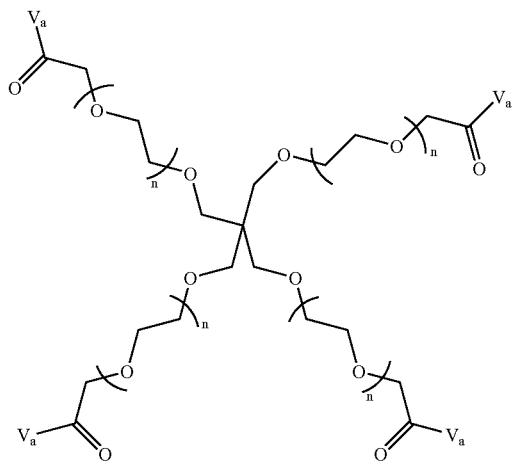
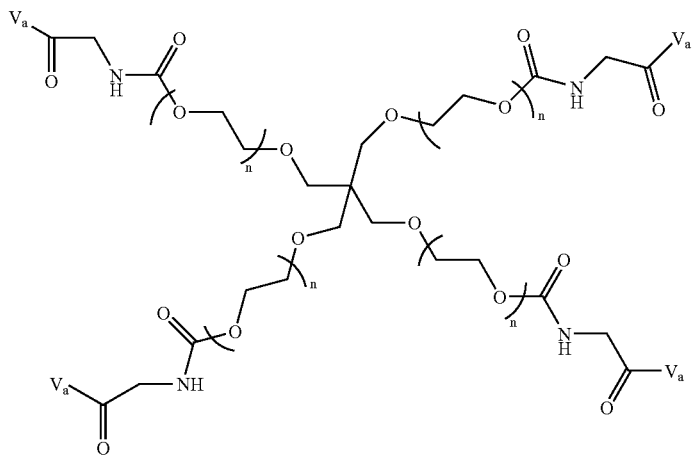

-continued
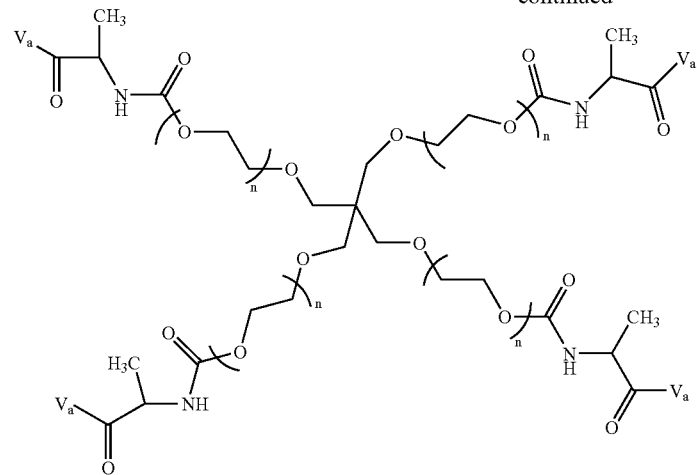
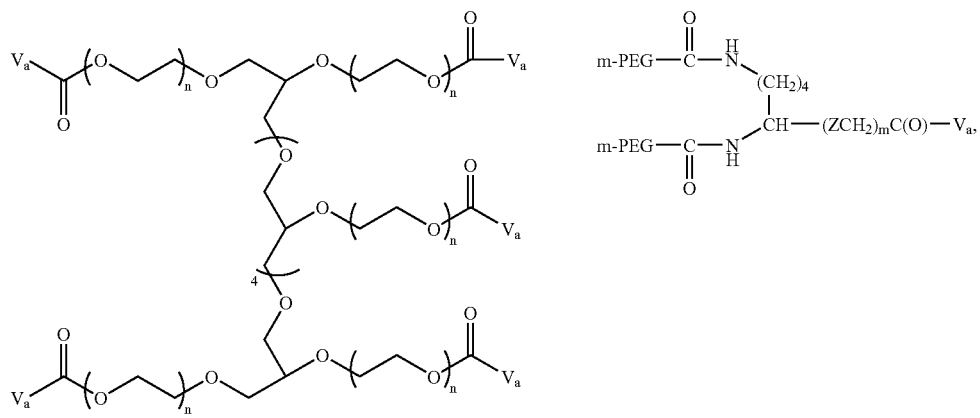
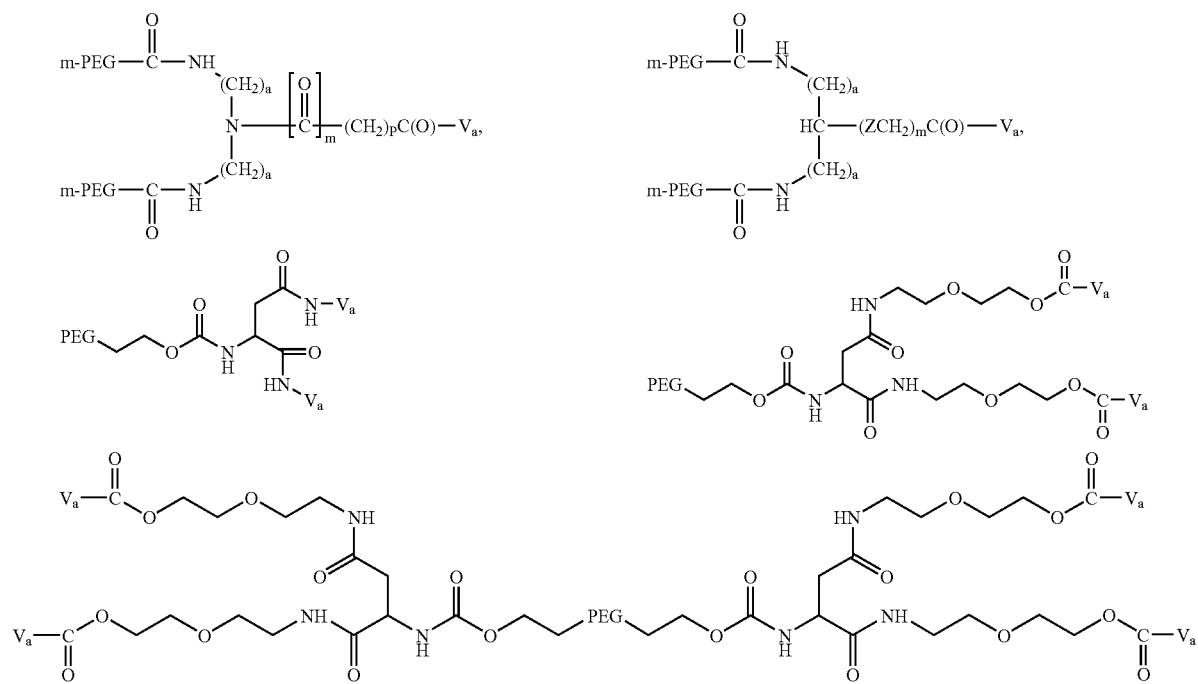

wherein:
mPEG is $CH_3-O-(CH_2CH_2O)_x-$;

(a) is an integer of from about 1 to about 5;
Z is O, $NR_8$, S, SO or $SO_2$, where $R_8$ is H, $C_{1-8}$ alkyl, $C_{1-8}$ branched alkyl, $C_{1-8}$ substituted alkyl, aryl or aralkyl;
(m) is 0 or 1;
(p) is a positive integer, from about 1 to about 6;
x is an integer from about 10 to about 2,300, and
$V_b$ is -continued

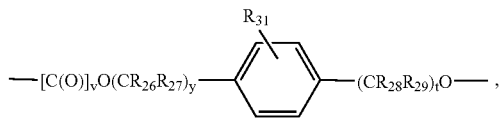

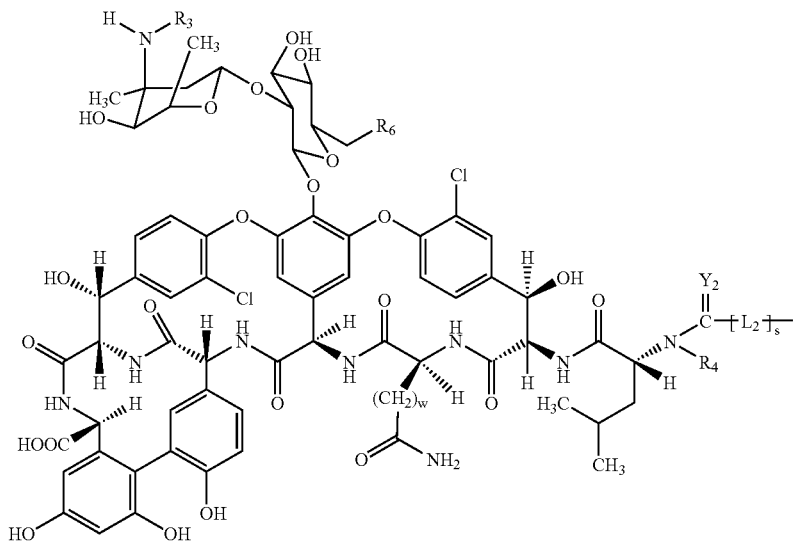

wherein:
$Y_2$ is O;
$L_2$ is a bifunctional linker selected from the group consisting of amino acids and —$[C(O)]_v NR_{25}(CR_{26}R_{27})_t$—,
—$[C(O)]_v (CR_{26}R_{27})_t$—,
—$[C(O)]_v NR_{25}(CR_{26}R_{27}O)_t$—,
—$[C(O)]_v NR_{25}(CR_{26}R_{27}O)_t(CR_{28}R_{29})_y O$—,
—$[C(O)]_v NR_{25}(CR_{26}R_{27}O)_t(CR_{28}R_{29})_y$—,
—$[C(O)]_v NR_{25}(CR_{26}R_{27})_t O$—,
—$[C(O)]_v NR_{25}(CR_{26}R_{27})_t(CR_{28}R_{29}O)_y NR_{30}$—,
—$[C(O)]_v O (CR_{26}R_{27})_t NR_{30}$—,
—$[C(O)]_v O (CR_{26}R_{27})_t O$—,
—$[C(O)]_v NR_{25}(CR_{26}R_{27})_t NR_{30}$—,
—$[C(O)]_v NR_{25}(CR_{26}R_{27})_t(CR_{28}R_{29})_y$—,
—$[C(O)]_v NR_{25}(CR_{26}R_{27}O)_t(CR_{28}R_{29})_y NR_{30}$—,
—$[C(O)]_v O(CR_{26}R_{27}O)_t NR_{30}$—,

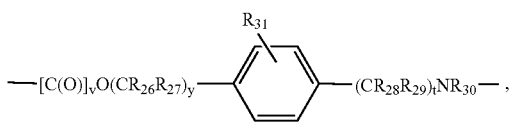

-continued

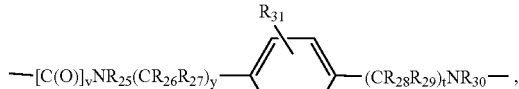

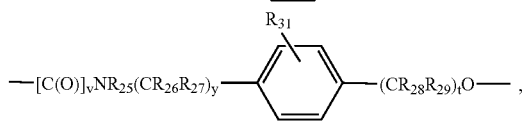

wherein:
$R_{25}$-$R_{30}$ are independently selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxyalkyl, phenoxyalkyl and $C_{1-6}$ heteroalkoxys;

$R_{31}$ is selected from the group consisting of hydrogen, $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxyalkyl, phenoxyalkyl and $C_{1-6}$ heteroalkoxys, $NO_2$, haloalkyl and halogen;

t and y are individually selected positive integers ranging from about 1 to about 4, and v is 0 or 1;

$R_3$ and $R_4$ are each independently hydrogen or $CH_3$;

$R_6$ is OH or NH-aryl;

s is 0-2;

e is 0 or 1; and w is 1.

18. A compound of claim 13 having the formula:

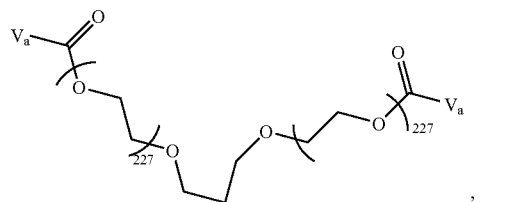

,

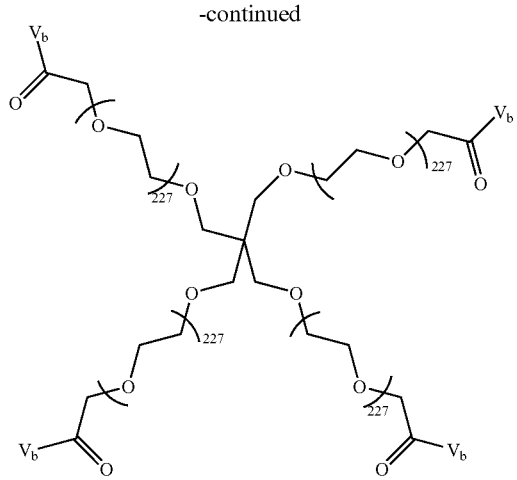

,

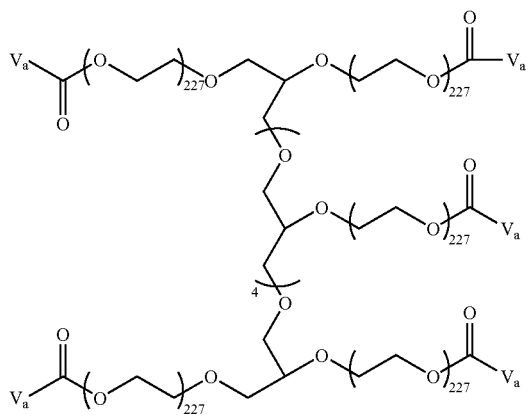

and

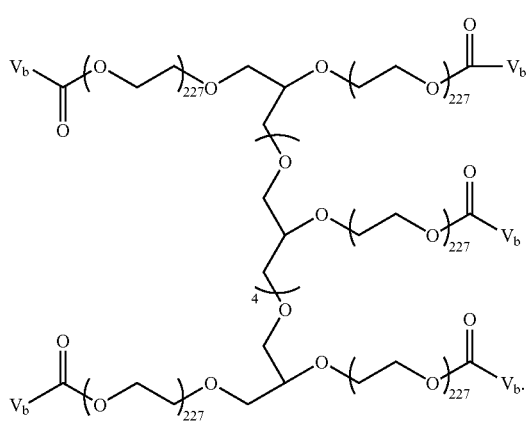

.

wherein
$V_a$ is
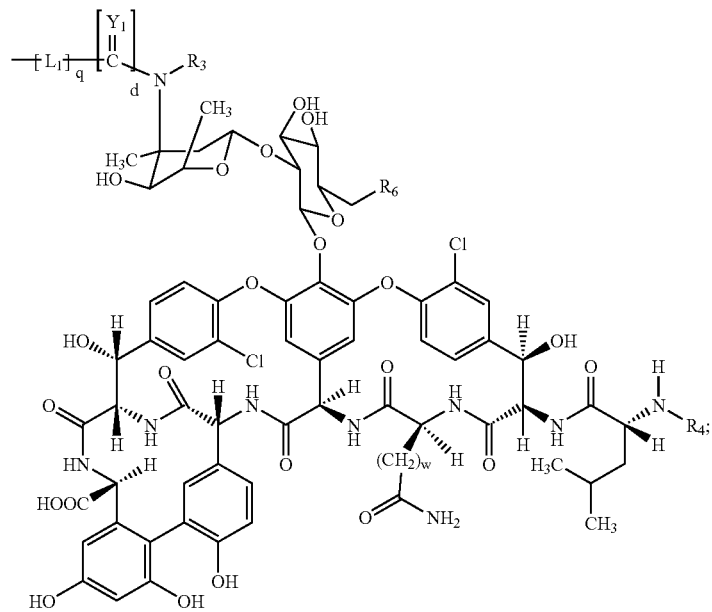
and
$V_b$ is
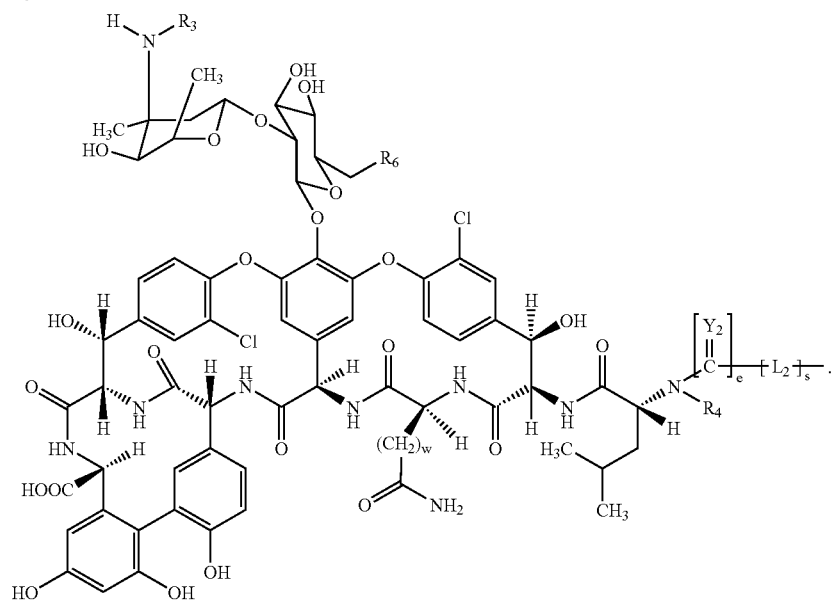

19. A process for preparing a compound of claim 1 comprising, reacting a vancomycin compound of the formula:

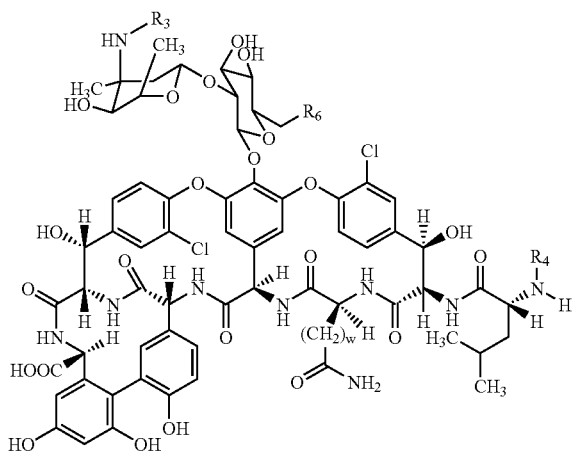

$R_3$ and $R_4$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ hetero-alkyls, substituted $C_{1-6}$ hetero-alkyls, $C_{1-6}$ alkoxyalkyl, phenoxyalkyl and $C_{1-6}$ heteroalkoxys;

$R_6$ is OH, NH-aryl, NH-aralkyl, or NH—$C_{1-12}$alkyl; and w is 1 or 2;

with a polymer residue containing at least one leaving group capable of reacting with the sugar amino group of said vancomycin compound in the presence of at least about a twentyfold molar excess of triethylamine and a sufficient amount of dimethylformamide.

20. The process of claim 19 further comprising reacting said sugar amino compound with a second activated polymer residue containing at least one leaving group capable of reacting with the N-methyl-amino group of said compound in the presence of at least about a 5 fold molar excess of dimethylaminopyridine and a sufficient amount of a solvent mixture of dichloromethane and dimethylformamide.

21. The process of claim 20, wherein said solvent mixture comprises about equal parts dichloromethane and dimethylformamide.

22. A method of treating a bacterial infection in a mammal comprising administering an effective amount of a compound of claim 1, to a mammal in need of such treatment, whereby, the compound of claim 1 undergoes degradation and releases vancomycin in vivo.

23. A method of treating a bacterial infection in a mammal comprising administering an effective amount of a compound of claim 11, to a mammal in need of such treatment, whereby, the compound of claim 11 undergoes degradation and releases vancomycin in vivo.

24. A method of treating a bacterial infection in a mammal comprising administering to a mammal in need of such treatment, an effective amount of a combination of vancomycin or a pharmaceutically acceptable salt thereof, and a compound of claim 1.

25. A kit comprising in separate containers in a single package, pharmaceutical compositions for use in combination to treat a bacterial infection which comprises in one container a therapeutically effective amount of vancomycin or a pharmaceutically acceptable salt thereof in a pharmaceutically acceptable carrier and in a second container a therapeutically effective amount of a compound of claim 1 or a pharmaceutically acceptable salt thereof in a pharmaceutically acceptable carrier.

26. The compound of claim 11, wherein the amino acid is selected from the group consisting of alanine, valine, leucine, isoleucine, glycine, serine, threonine, methionine, cysteine, phenylalanine, tyrosine, tryptophan, aspartic acid, glutamic acid, lysine, arginine, histidine and proline.

27. The compound of claim 13, wherein the amino acid is selected from the group consisting of alanine, valine, leucine, isoleucine, glycine, serine, threonine, methionine, cysteine, phenylalanine, tyrosine, tryptophan, aspartic acid, glutamic acid, lysine, arginine, histidine and proline.

28. A method of treating a bacterial infection in a mammal comprising administering an effective amount of a compound of claim 13, to a mammal in need of such treatment, whereby, the compound of claim 13 undergoes degradation and releases vancomycin in vivo.

* * * * *

UNITED STATES PATENT AND TRADEMARK OFFICE
CERTIFICATE OF CORRECTION

PATENT NO. : 7,462,687 B2
APPLICATION NO. : 10/705740
DATED : December 9, 2008
INVENTOR(S) : Richard B. Greenwald et al.

It is certified that error appears in the above-identified patent and that said Letters Patent is hereby corrected as shown below:

a) <u>Column 43, lines 47-67 in claim 1</u>, the chemical formula should appear as:

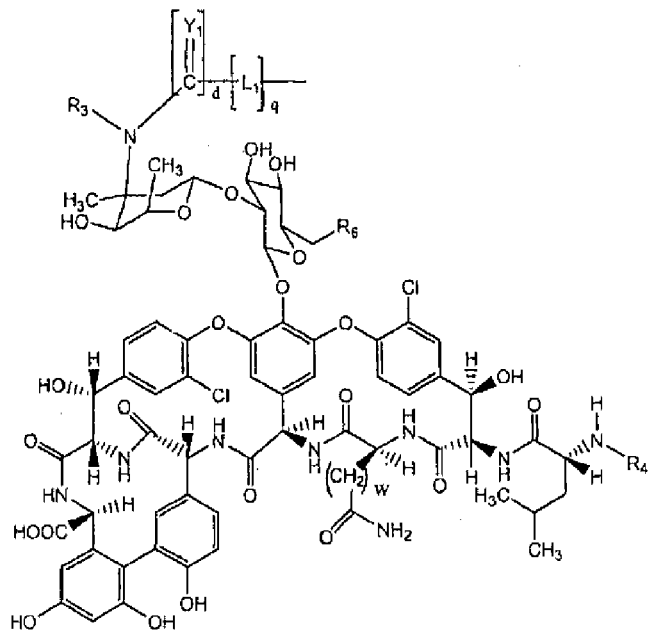

b) <u>Column 44, lines 43-59 in claim 1</u>, the chemical formula should appear as:

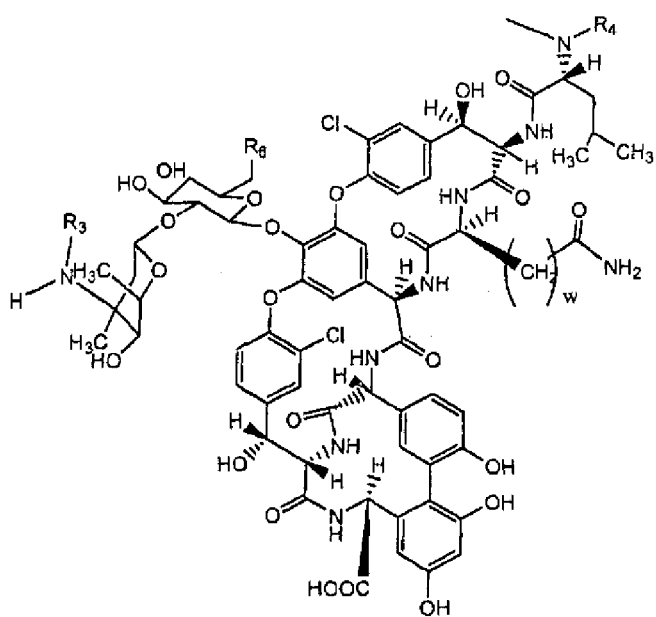

UNITED STATES PATENT AND TRADEMARK OFFICE
CERTIFICATE OF CORRECTION

PATENT NO.       : 7,462,687 B2
APPLICATION NO.  : 10/705740
DATED            : December 9, 2008
INVENTOR(S)      : Richard B. Greenwald et al.

It is certified that error appears in the above-identified patent and that said Letters Patent is hereby corrected as shown below:

c) <u>Column 45, line 21 in claim 1</u>, "$(CR_{26}R_{27}O)_t$" should read -- $(CR_{26}R_{27})_t$ -- d) <u>Columns 45-46, lines 39-62 in claim 2</u>, the chemical formula should appear as:

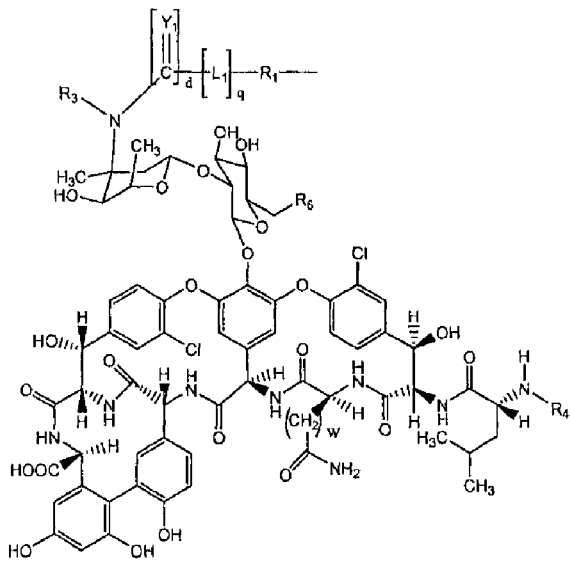

e) <u>Columns 49-50, lines 1-26 in claim 3</u>, the chemical formula should appear as:

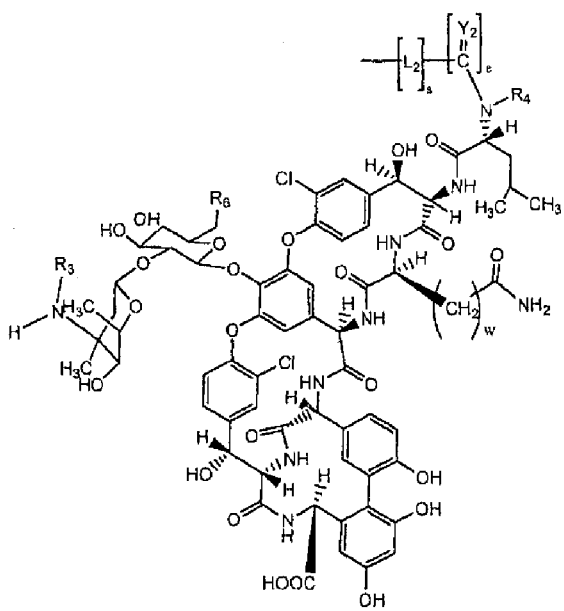

UNITED STATES PATENT AND TRADEMARK OFFICE
CERTIFICATE OF CORRECTION

PATENT NO. : 7,462,687 B2  
APPLICATION NO. : 10/705740  
DATED : December 9, 2008  
INVENTOR(S) : Richard B. Greenwald et al.

Page 3 of 9

It is certified that error appears in the above-identified patent and that said Letters Patent is hereby corrected as shown below:

f) <u>Column 49, line 50 in claim 7,</u>
  "O-(CH$_2$CH$_2$O)$_x$———" should read -- ———O-(CH$_2$CH$_2$O)$_x$——— -- g) <u>Columns 57-58, lines 47-65 in claim 16</u>, the chemical formulas should appear as:

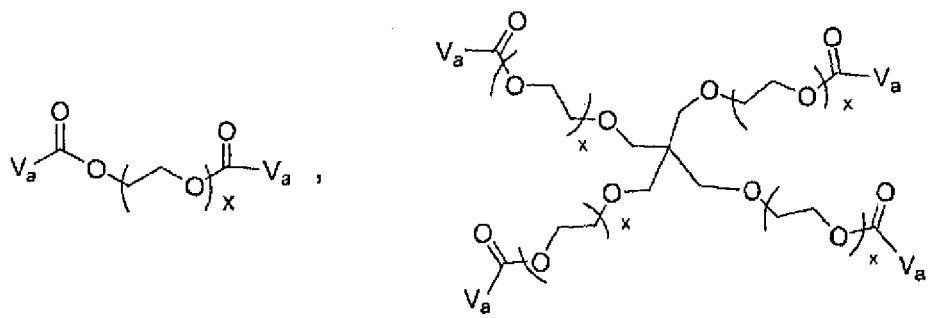

h) <u>Columns 59-60, claim 16</u>, the chemical formulas should appear as:

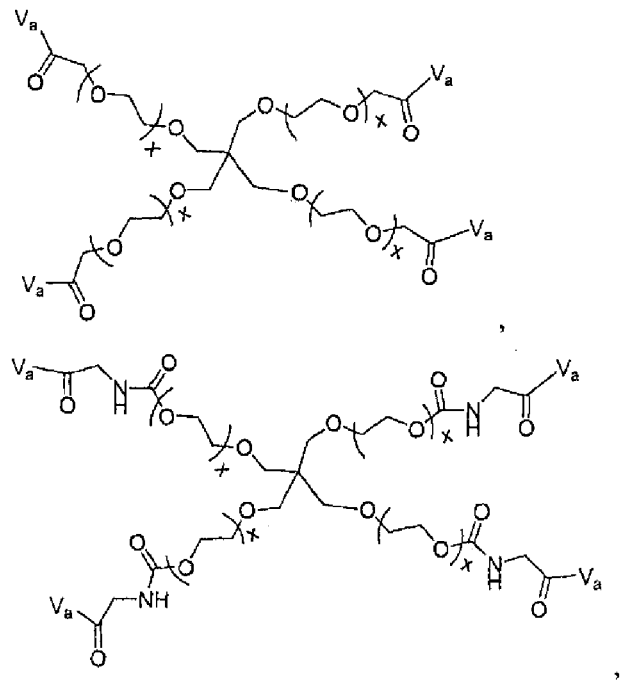

UNITED STATES PATENT AND TRADEMARK OFFICE
CERTIFICATE OF CORRECTION

PATENT NO. : 7,462,687 B2
APPLICATION NO. : 10/705740
DATED : December 9, 2008
INVENTOR(S) : Richard B. Greenwald et al.

It is certified that error appears in the above-identified patent and that said Letters Patent is hereby corrected as shown below:

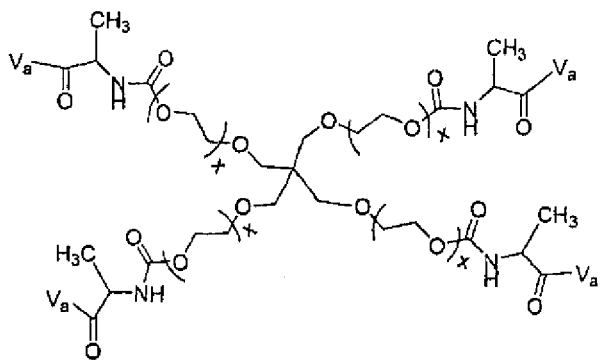

, i) <u>Columns 61-62, claim 16</u>, the chemical formulas should appear as:

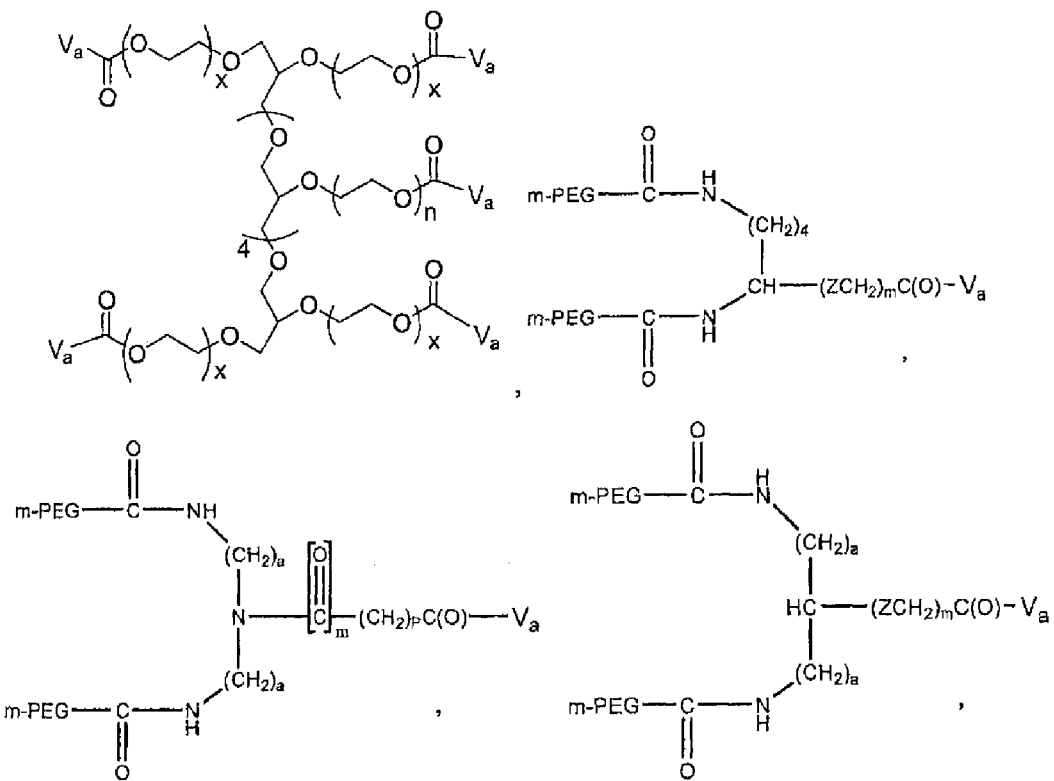

UNITED STATES PATENT AND TRADEMARK OFFICE
CERTIFICATE OF CORRECTION

PATENT NO. : 7,462,687 B2
APPLICATION NO. : 10/705740
DATED : December 9, 2008
INVENTOR(S) : Richard B. Greenwald et al.

It is certified that error appears in the above-identified patent and that said Letters Patent is hereby corrected as shown below:

j) <u>Columns 65-66, claim 17</u>, the chemical formulas should appear as:

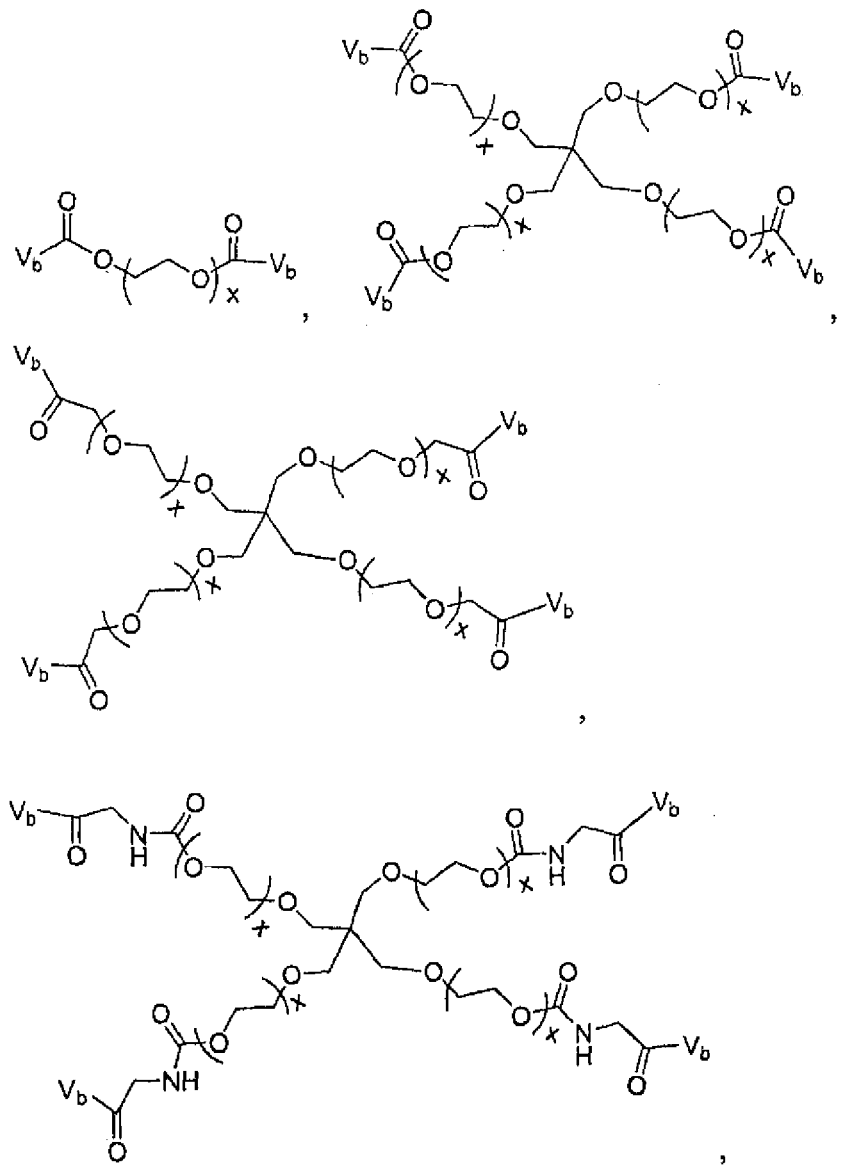

UNITED STATES PATENT AND TRADEMARK OFFICE
CERTIFICATE OF CORRECTION

PATENT NO. : 7,462,687 B2
APPLICATION NO. : 10/705740
DATED : December 9, 2008
INVENTOR(S) : Richard B. Greenwald et al.

It is certified that error appears in the above-identified patent and that said Letters Patent is hereby corrected as shown below:

k) Columns 67-68, claim 17, the chemical formulas should appear as:

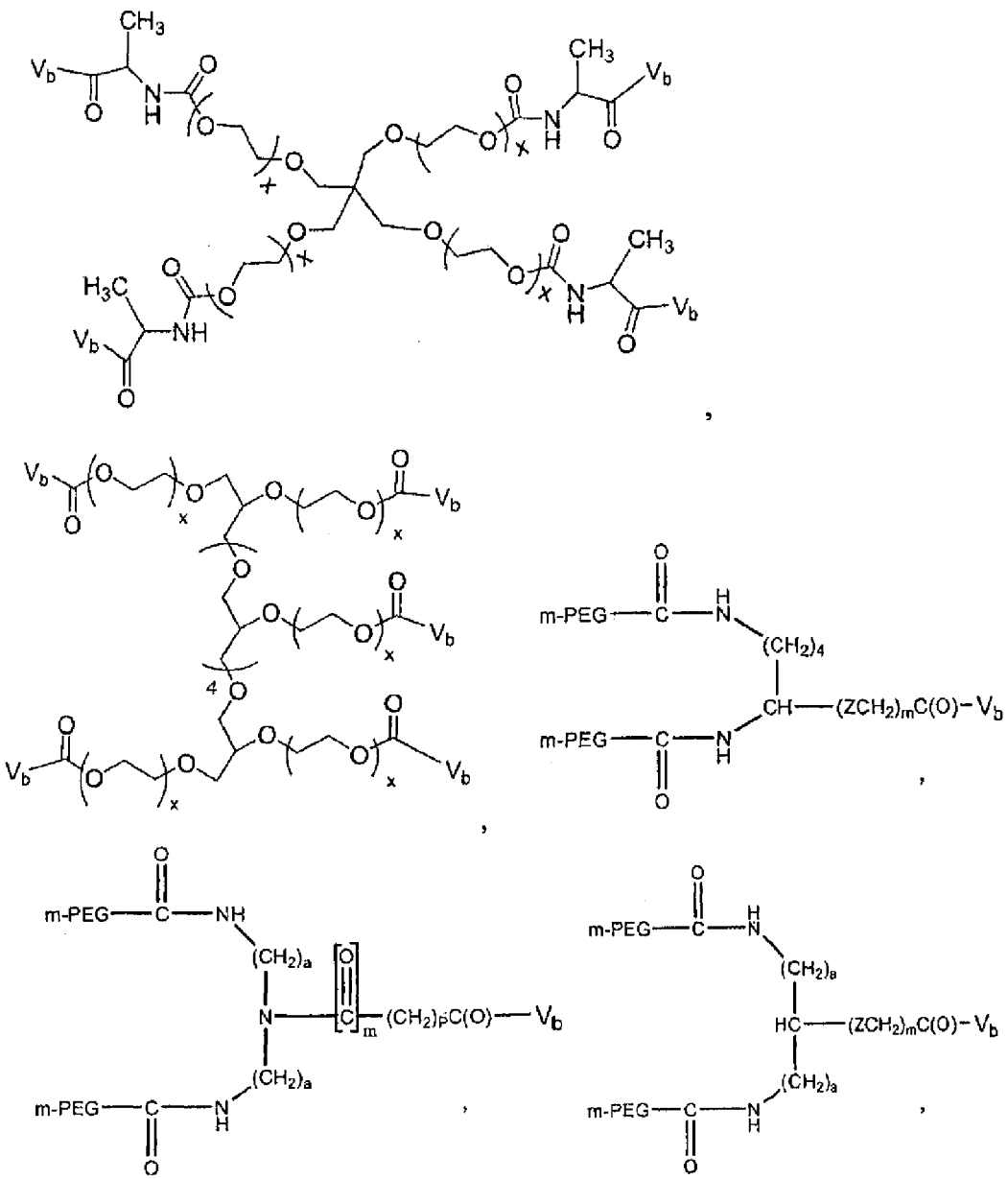

UNITED STATES PATENT AND TRADEMARK OFFICE
CERTIFICATE OF CORRECTION

PATENT NO. : 7,462,687 B2
APPLICATION NO. : 10/705740
DATED : December 9, 2008
INVENTOR(S) : Richard B. Greenwald et al.

It is certified that error appears in the above-identified patent and that said Letters Patent is hereby corrected as shown below:

1) <u>Columns 69-70, lines 12-38 in claim 17</u>, the chemical formula should appear as:

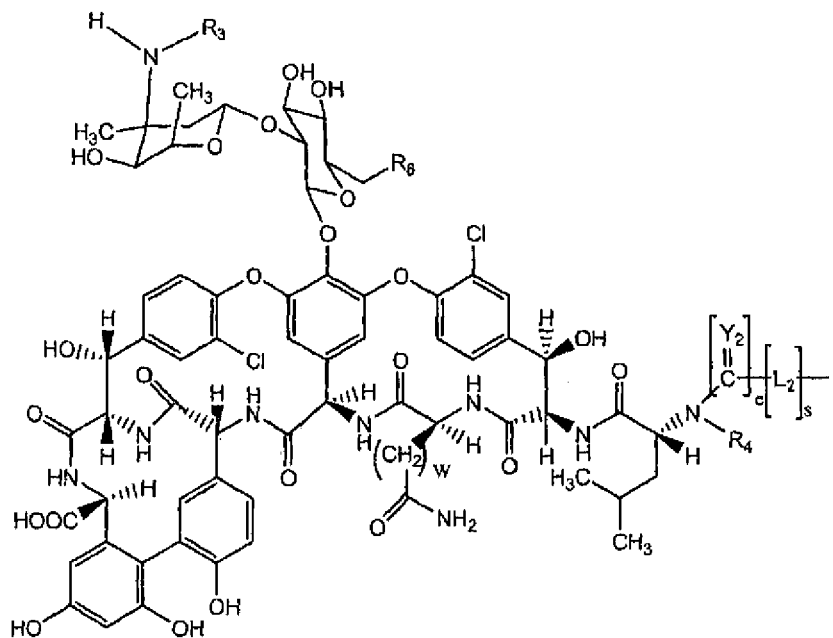

UNITED STATES PATENT AND TRADEMARK OFFICE
CERTIFICATE OF CORRECTION

PATENT NO. : 7,462,687 B2
APPLICATION NO. : 10/705740
DATED : December 9, 2008
INVENTOR(S) : Richard B. Greenwald et al.

It is certified that error appears in the above-identified patent and that said Letters Patent is hereby corrected as shown below:

m) <u>Columns 73-74, lines 2-35 in claim 18</u>, the chemical formula should appear as:

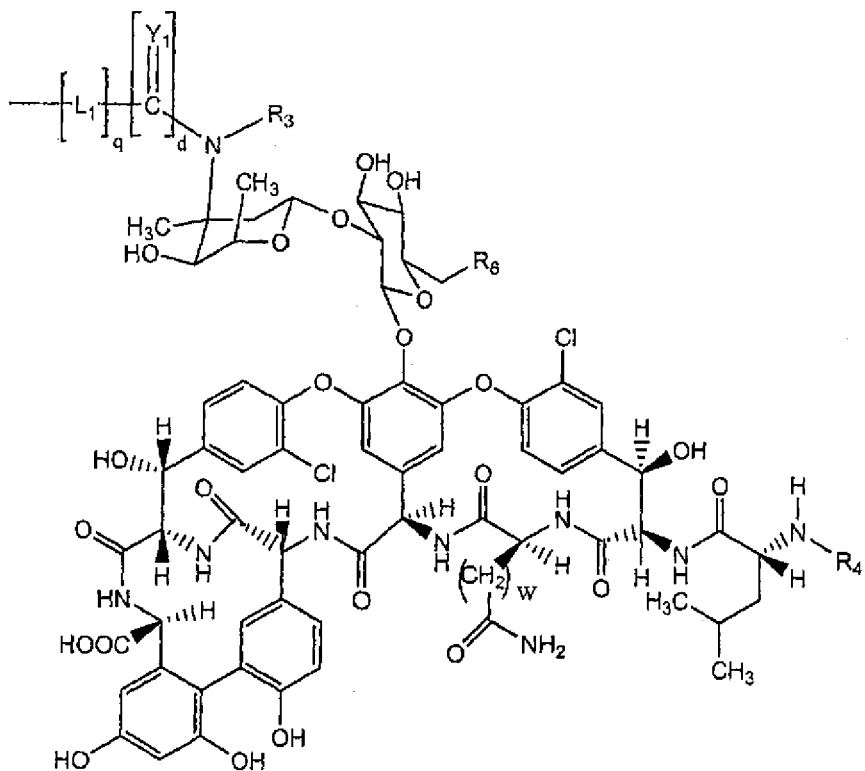

UNITED STATES PATENT AND TRADEMARK OFFICE
CERTIFICATE OF CORRECTION

PATENT NO. : 7,462,687 B2
APPLICATION NO. : 10/705740
DATED : December 9, 2008
INVENTOR(S) : Richard B. Greenwald et al.

It is certified that error appears in the above-identified patent and that said Letters Patent is hereby corrected as shown below:

n) Column 75, line 24 in claim 19, insert -- wherein -- before "$R_3$ and $R_4$ are"

Signed and Sealed this

Fifteenth Day of December, 2009

David J. Kappos
*Director of the United States Patent and Trademark Office*